United States Patent [19]
Okamura et al.

[11] 4,318,916
[45] Mar. 9, 1982

[54] ANTIBIOTIC PS-5 AND DERIVATIVES HAVING β-LACTAMASE INHIBITORY ACTIVITY AND PRODUCTION THEREOF

[75] Inventors: Kazuhiko Okamura, Yamato; Shoji Hirata, Fujisawa; Yasushi Okumura; Yasuo Fukagawa, both of Kamakura; Yasutaka Shimauchi, Ninomiya; Tomoyuki Ishikura, Chigasaki; Kageaki Kouno, Ikegami oto, all of Japan; Joseph Lein, Fayetteville, N.Y.

[73] Assignee: Sanraku-Ocean Co., Ltd., Tokyo, Japan

[21] Appl. No.: 882,730

[22] Filed: Mar. 2, 1978

[30] Foreign Application Priority Data

Mar. 31, 1977 [JP] Japan .................................. 52-35375
Aug. 9, 1977 [JP] Japan .................................. 52-94651

[51] Int. Cl.³ .................. C07D 487/09; A61K 31/40
[52] U.S. Cl. ............................. 424/274; 260/245.2 T; 424/114
[58] Field of Search .................... 260/326.31, 245.2 T; 424/274

[56] References Cited

U.S. PATENT DOCUMENTS

| 3,928,569 | 1/1975  | Umezawa et al.   | 424/117      |
| 3,950,357 | 4/1976  | Kahan et al.     | 260/326.31   |
| 4,141,986 | 2/1979  | Cassidy et al.   | 260/245.2 T  |
| 4,162,323 | 7/1979  | Kahan            | 260/245.2 T  |
| 4,162,324 | 7/1979  | Cassidy et al.   | 260/245.2 T  |
| 4,165,379 | 8/1979  | Kahan et al.     | 260/245.2 T  |
| 4,235,922 | 11/1980 | Ratcliffe et al. | 260/245.2 T  |

FOREIGN PATENT DOCUMENTS 2513855 10/1975 Fed. Rep. of Germany ........................ 260/326.31

OTHER PUBLICATIONS

Albers–Schönberg et al.; J.A.C.S., vol. 100, pp. 472–780, (9/27/78).
Derwent Abstracts, 67720w, 67721w, (3/27/75), 72840w, (4/18/75), 40282y, 40283y, 40280y, 40279y, 40281y, (11/19/76), 34505y, 34507y, (11/16/76), 72175x, (3/16/75).

Primary Examiner—Mary C. Lee
Attorney, Agent, or Firm—M. R. Johnson

[57] ABSTRACT

A novel antibiotic substance and derivatives thereof, having strong antibiotic activity and β-lactamase inhibiting effect and a method for producing the same by aerobic cultivation of Streptomyces A 271.

15 Claims, 7 Drawing Figures

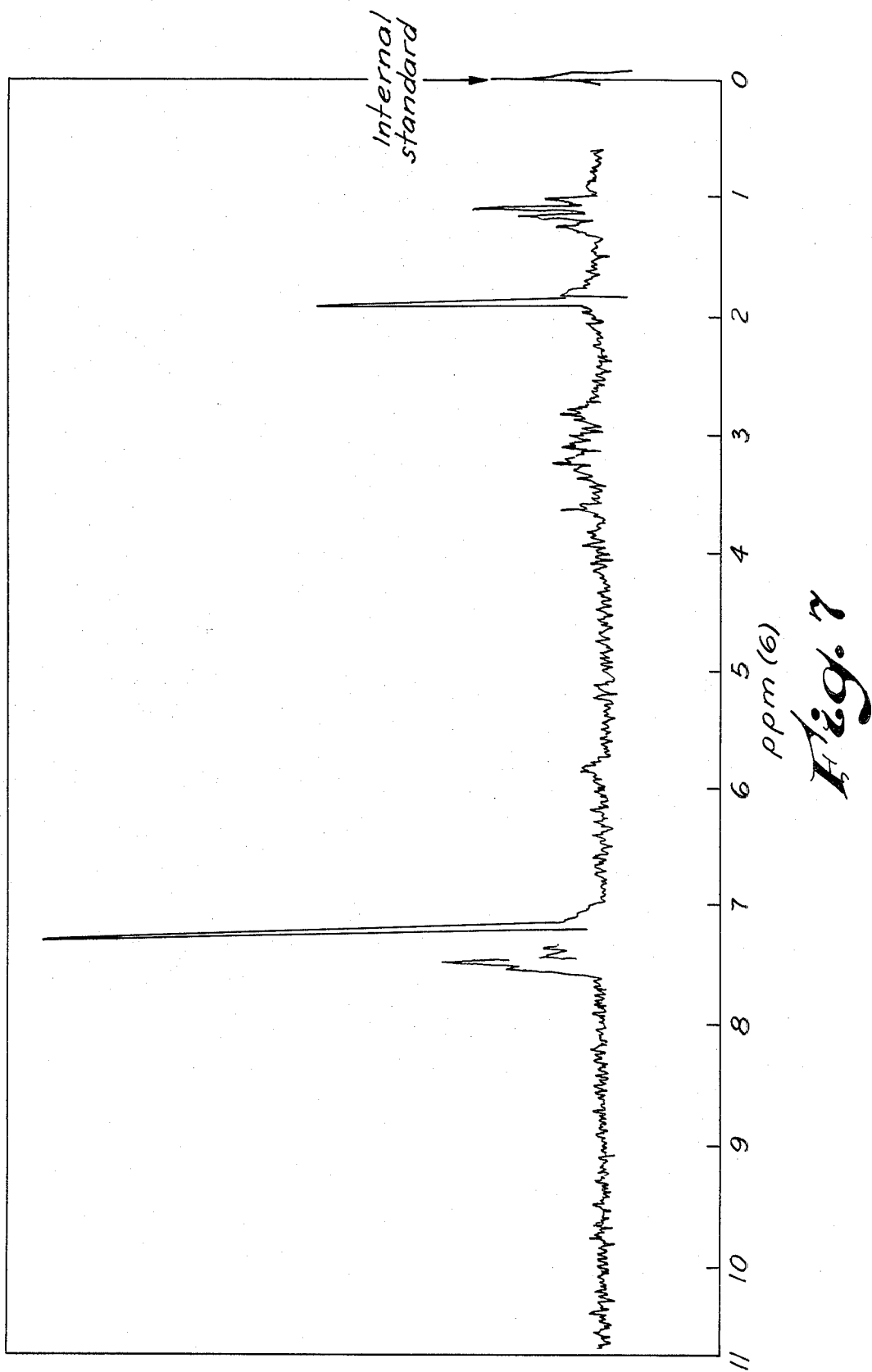

ANTIBIOTIC PS-5 AND DERIVATIVES HAVING β-LACTAMASE INHIBITORY ACTIVITY AND PRODUCTION THEREOF

BACKGROUND OF THE INVENTION

Some antibiotics having β-lactamase inhibitory activity or β-lactamase inhibitory agents have so far been known. For example, the following have been reported: MC696-SY2-A and B isolated from the culture broth of the MC696-SY2 producing strain belonging to the genus Streptomyces (U.S. Pat. No. 3,928,569: Derwent CPI 15846V), MM4550 or MM13902 isolated from the cultured materials of the MM4550 or MM13902 producing strain which belongs to the genus Streptomyces (German Appln. DOS No. 2,513,855: Derwent CPI 67221W; German Appln. DOS No. 2,513,854: Derwent CPI 67720W), clavulanic acid isolated from the cultured materials of Streptomyces clavuligerus (German Appln. DOS No. 2,517,316: Derwent CPI 72840W), and the like. The antibiotic thienamycin having a penicillin-like chemical skeleton and the derivatives thereof have also been reported (U.S. Pat. No. 3,950,357: Derwent CPI 31696X; German Appln. DOS No. 2,652,677: Derwent CPI 40282Y; Belgian Pat. No. 848,346: Derwent CPI 34505Y; Belgian Pat. No. 848,349: Derwent CPI 34507: German Appln. DOS No. 2,652,680: Derwent CPI 40283Y; German Appln. DOS No. 2,652,675: Derwent CPI 40280Y: German Application DOS No. 2,652,674: Derwent CPI 40279Y; German Appln. DOS No. 2,652,676: Derwent CPI 40281Y).

SUMMARY OF THE INVENTION

This invention relates to a new antibiotic and the derivatives thereof. More particularly, it is concerned with a novel antibiotic defined as PS-5 and the derivatives thereof, which have strong antibiotic activity, β-lactamase inhibitory activity and ability to synergistically enhance the antibiotic activity of penicillins, cephalosporins or the like against β-lactamase producers, and it is concerned with the method for producing these novel antibiotic substances and with the antibiotic compositions containing said substances.

The first object of the present invention is to provide the new antibiotic substance PS-5 having both strong antibiotic activity and β-lactamase inhibitory activity.

The second object of the present invention is to provide derivatives, particularly the trityl derivative, of said antibiotic PS-5 which also shows strong antibiotic activity and β-lactamase inhibitory activity.

Another object of this invention is to show that the new antibiotic PS-5 and the trityl derivative thereof, also have the ability to synergistically enhance the antibiotic activity of penicillins, cephalosporins or the like against β-lactamase-producing resistant bacteria.

Another object of this invention is to provide the methods for producing the antibiotic PS-5 by a fermentation process and to provide a pure culture of a microorganism capable of producing the same.

Another object of this invention is to provide methods for producing the derivatives of the antibiotic PS-5, and more particularly, the trityl derivative.

A further object of this invention is to provide preventive and therapeutic methods and compositions of the antibiotic PS-5 or its trityl derivative for use in infectious diseases caused by Gram-positive and Gram-negative bacteria, including synergic combinations with penicillins, cephalosporins and other β-lactamase sensitive antibiotics. Other objectives of this invention will become apparent from the following description.

The antibiotic PS-5 can be produced by a process which comprises cultivating an antibiotic PS-5 producing microorganism in a nutrient medium and isolating the antibiotic PS-5.

Representative microorganisms of the above mentioned antibiotic PS-5 producing strains belong to the genus Streptomyces. As the most suitable example, is herein described a Streptomyces strain which was isolated from soil sample collected near Eiheiji Temple in the Yoshida District of Fukui Prefecture in Japan and given the strain number A271.

Taxonomical characteristics of Strain A271

The taxonomical characteristics of strain Streptomyces A271 are as follows:

(1) Morphological characteristics

Branching of sporulated aerial mycelium: Simply branched. Form of sporulated aerial mycelium: Top of aerial mycelium shows hooks, loops or uncomplete spirals.

This is considered to belong to the Section Retinaculum-Apertum. These forms are particularly observed when cultivated on oatmeal agar medium and glycering-asparagine agar medium, while a straight or flexuous form is occasionally observed on yeast extract-malt extract agar medium. Form and number in chain of spores: Oval or cylindrical spores forming a chain of more than 10 (usually 10 to 50) spores. Size and surface structure of spores: $0.8-1.0 \times 1.0-1.8\mu$, smooth surface. Neither flagella nor sporangium has been observed. Hyphae are formed on aerial mycelium.

(2) Cultural characteristics

Cultural characteristics of the strain A271 are shown in Table 1, in which observation results after 2 weeks cultivation at 28° C. are shown unless noted otherwise. Expression of color tone is mainly based on the method of H. D. Tresner and E. J. Backus' "System of color wheels for Streptomycete taxonomy", (see Appl.Microbiol. 11, 335, 1963) and the color tone code in "Guide to Color Standard" published by Japan Color Institute Foundation.

TABLE 1

| Media | Growth | Color of Aerial Mycelium | Color of Substrate Mycelium | Soluble Pigment |
| --- | --- | --- | --- | --- |
| Sucrose-nitrate agar medium | abundant | light orange yellow (3ea) | light yellow (2fb) to light orange yellow (3ea) | none |
| Glucose-asparagine agar medium | abundant | pale orange yellow (3ca) to light orange yellow (3ea) | light yellow (1½ fb)- 2fb) | none |
| Glycerin-asparagine agar medium | abundant | pale orange yellow (3ca) to light orange yellow (3ea) | light yellow (2fb) to somewhat yellowish pink (4gc) | none |
| Starch inorganic salt agar medium | abundant | pale orange yellow (3ca) to light orange yellow (3ea) | light orange yellow (3ea) to light yellow (2fb) | none |
| Tyrosine agar medium | abundant | pale orange yellow (3ca) to light | light orange yellow (3ea) to brownish | none |

TABLE 1-continued

| Media | Growth | Color of Aerial Mycelium | Color of Substrate Mycelium | Soluble Pigment |
|---|---|---|---|---|
| | | orange yellow (3ea) | yellow | |
| Nutrient agar medium | abundant | hardly formed; if formed, somewhat dark | pale yellow (2db) | none |
| Yeast extract-malt extract agar medium | abundant | pale orange yellow (3ca) to light orange yellow (3ea) | light orange yellow (3ea) to pale brown (4ie) | none |
| Oatmeal agar medium | abundant | pale orange (3ca) to light orange | light yellow (2fb) | none |

(3) Physiological characteristics (1) Growth temperature range: 10°–40° C., optimum 20°–30° C.
(2) Liquefaction of gelatin (on glucose-peptone-gelatin medium): liquefied (cultured at 20° C.)
(3) Hydrolysis of starch (on starch inorganic salt agar medium): hydrolyzed
(4) Coagulation and peptonization of skimmed milk: peptonized but no coagulation observed
(5) Formation of melanoid pigment: no melanoid pigment formed on tyrosine agar medium and peptone yeast iorn agar medium and in tryptone-yeast extract broth
(6) Utilization of the following various carbon sources (Pridham and Gottlieb agar medium):

| | |
|---|---|
| L-Arabinose | + |
| D-Xylose | + |
| D-Glucose | + |
| D-Fructose | − |
| Sucrose | ± |
| Inositol | − |
| L-Rhamnose | + |
| Raffinose | − |
| D-Mannitol | − |

(+: well utilized, ±: slightly utilized, −: very slightly utilized or not at all).

It is obvious from the above characteristics that the strain A271 belongs to the genus Streptomyces and shows characteristics shared by microorganisms belonging to Section RA, since the color tone of the mycelium surface is yellow or red, the spore surface is smooth and no water soluble pigment like melanoid pigemnt is formed. Cultures having such taxonomical characteristics were looked for in Waksman's "The Actinomycetes" vol. 2"(1961), E. B. Shirling and D. Gottlieb's papers in International Journal of Systematic Bacteriology vol. 18, page 69–189 (1968), ibid., page 279–892 (1968), ibid., vol. 19, page 391–512 (1969), ibid., vol. 22, page 265–394 (1972), and Bergey's Mannual of determinative Bacteriology, 8th edition (1974). Similar cultures belonging to Section RA were found to be *Actinomyces cremeus, Actinomyces flavidovirens, Actinomyces albohelvatus, Actinomyces flavescens, Streptomyces rutgersensis, Streptomyces chryseus, Streptomyces helvaticus*. As one of the resembling cultures *Streptomyces pluricolorescens was also selected, based on its morphological characteristics although it belongs to the Section RF.* These 8 cultures except the last *Streptomyces pluricolorescens* were reported to produce aerial mycelium having a straight form or loops, the variation being dependent on the cultural conditions. Type cultures of the above 8 species were compared with the strain A271 of this invention after cultivation under the same conditions. From the results, strain A271 is clearly discriminated from these cultures with differences on growth, color of aerial mycelium and color of substrate mycelium as well as marked differences on utilization of carbon sources.

In table 2, 3 and 4, are given the results of the comparison of strain A271 with the two cultures most closely resembling it.

TABLE 2

Comparison with the resembling cultures
Color of aerial mycelium

| Media | Strain A271 | Actinomyces cremeus ISP 5147 | Actinomyces flavidovirens ISP 5150 |
|---|---|---|---|
| Sucrose nitrate agar medium | light orange yellow (3ea) | hardly formed | not formed |
| Glucose-asparagine agar medium | pale orange yellow (3ca) to light orange yellow (3ea) | pale orange yellow (3ca) | white (b) |
| Glycerin-asparagine agar medium | pale orange yellow (3ca) to light orange yellow (3ea) | pale orange yellow (3ca) | hardly formed; if formed slightly, white (a) |
| Starch inorganic agar medium | pale orange yellow (3ca) to light orange (3ea) | pale orange yellow (3ca) | thinly formed white (a) to pale yellow (2db) |
| Nutrient agar medium | hardly formed, if formed somewhat dark | white (a) to pale orange yellow (3ca) | white |
| Yeast extract-malt extract agar medium | pale orange yellow (3ca) to light orange yellow (3ea) | pale yellow (2db) | white (b) to pale yellowish green (1cb) |
| Oatmeal agar medium | pale orange yellow (3ca) to light orange yellow (3ea) | white (b) to pale orange yellow (3ca) | white (b) to pale yellowish green (1bd) |

TABLE 3

Comparison with the resembling cultures
Color of substrate mycelium

| Media | Strain A271 | Actinomyces cremeus ISP 5147 | Actinomyces flavidovirens ISP 5150 |
|---|---|---|---|
| Sucrose-nitrate agar medium | light yellow (2fb) to light orange yellow (3ea) | poor growth colorless to white (b) | poor growth colorless to white (a) |
| Glucose-asparagine agar medium | light yellow (1½ fb - 2fb) | light orange yellow (3ea) | pale yellow (2db) |
| Glycerin-asparagine agar medium | light yellow (2fb) to somewhat yellowish pink (4gc) | light orange yellow (3ea) | grayish yellow (3ec) |
| Starch-inorganic salt agar medium | light orange yellow (3ea) to light yellow (2fb) | moderate yellowish pink (4ea) | light yellow (2fb) |
| Tyrosine agar medium | light orange yellow (3ea) to brownish yellow | pale brown (4ie) | grayish yellow (3ec) |
| Nutrient agar medium | pale yellow (2db) | light orange yellow (3ea) | pale yellow (2db) |

TABLE 3-continued

Comparison with the resembling cultures
Color of substrate mycelium

| Media | Strain A271 | Actinomyces cremeus ISP 5147 | Actinomyces flavidovirens ISP 5150 |
|---|---|---|---|
| Yeast extract-malt extract agar medium | light orange yellow (3ea) to pale brown (4ie) | light orange yellow (3ea) to dark yellow | dull yellow |
| Oatmeal agar medium | light yellow (2fb) | somewhat yellowish pink (4gc) | pale yellow (2db) to pale orange yellow (3ca) |

TABLE 4

Comparison with the resembling cultures
Utilization of carbon sources

| Carbon Sources | Strain A271 | Actinomyces cremeus ISP 5157 | Actinomyces flavidovirens ISP 5150 |
|---|---|---|---|
| Arabinose | + | + | + |
| D-xylose | + | + | + |
| D-Glucose | + | + | + |
| D-Fructose | − | + | + |
| Sucrose | ± | − | − |
| Inositol | − | − | + |
| L-Rhamnose | + | − | + |
| Raffinose | − | − | − |
| D-Mannitol | − | − | − |

The following considerations come out from the results shown in the above Tables: concerning the color of aerial mycelium: *Actinomyces flavidovirens* is generally white but when it is yellow, it is greenish yellow, being clearly different from the strain A271 of this invention, and *Actinomyces cremeus* generally shows a weaker reddish tone of the pale orange yellow color than that of the strain A271, being clearly discriminated from the Strain A271.

Concerning the color of substrate mycelium, *Actinomyces flavidovirens* shows pale yellow color and *Actinomyces cremeus* shows light orange yellow color in many cases, while the Strain A271 generally shows light yellow color. Furthermore, detailed comparison of the experimental results obtained in various media definitely shows that the Strain A271 is different from the other two cultures. The strain A271 differs from *Actinomyces cremeus* on the utilization of D-fructose and L-rhamnose and from *Actinomyces flavidovirens* on the utilization of D-fructose and inositol.

Accordingly, the strain A271 of this invention is clearly different from the two known cultures most closely resembling it.

Consequently, the strain A271 is different from all known Streptomycetes species and is recognized as a new species, which is designated as Streptomyces sp. A271. This culture has been deposited with the Fermentation Research Institute, Agency of Industrial Science and Technology where it has been assigned the culture number FERM-P No. 3984. A sample of the Streptomyces sp. A271 was also deposited with the ATCC wherein it has been assigned the collection No 31358.

In this invention, one can use not only the Strain A271 itself but also the natural mutants and artificial mutants thereof which may be induced by chemical or physical treatments.

The antibiotic PS-5 producers can be selected from a wide range of microorganisms which are not limited to a particular genus.

Selection of the microorganisms producing PS-5 can be carried out by the following method by a person who is skilled in the art.

Cultured broth filtrates of microorganisms isolated from soil are analyzed by using bioassay agar plate inoculated with a β-lactam susceptible microorganisms and another bioassay agar plate containing β-lactamase and inoculated with the same organism. The microorganisms giving broth filtrates which show smaller inhibitory zones on the latter bioassay plate than that on the former bioassay plate are selected for further work. Then, the active components in the cultured broth of the microorganisms selected by the above method are adsorbed on activated carbon and then eluted. The concentrated eluates are developed by paper chromatography or thin layer chromatography which are followed by bioautography with a β-lactam susceptible microorganism as the assay organism. The screening method is more concretely explained by the following example. The Comamonas bioassay plate which will be described later is employed as the bioassay agar plate inoculated with β-lactam susceptible assay organism. The Comamonas CV bioassay plate and the Comamonas CM bioassay plate are prepared by adding to the above Comamonas bioassay plate the β-lactamase produced by *Proteus vulgaris* P-5 and *Citrobacter freundii* E-9 respectively.

Pulp discs of 8 mm diameter added with the cultured broth filtrates of microorganisms isolated from soil are placed on the above bioassay plates and the plates are incubated at 35° C. for 20 hours.

After the incubation, the microorganisms whose broth filtrate gave an inhibitory zone on the Comamonas bioassay plate and a smaller inhibitory zone on the Comamonas CV bioassay plate or the Comamonas CM bioassay plate are chosen.

To the broth filtrates of those microorganisms, 2% (W/V) amount of activated carbon ("Tokusei Shirasagi", Takeda Chemical Industries, Ltd.) is added and after stirring for 15 minutes, the insoluble material is collected by centrifugation. The insoluble material is washed with distilled water of the same volume as the broth filtrate used and collected again by centrifugation. The washed insoluble material is eluted by adding 50% (V/V) aqueous acetone of a half volume of the broth filtrate used and stirring at room temperature for 30 min. After centrifugation, the supernatant is evaporated at 30° C.–35° C. by using a rotary evaporator to obtain a 20-fold concentrated solution as compared with the broth filtrate used. The concentrated solution is subjected to descending paper chromatography with filter paper (Toyo Filter Paper, Toyo Roshi Kaisha Ltd.) by developing for 16 hours with 30% acetonitrile/Tris EDTA solvent (composed of 120 ml acetonitrile, 80 ml pH 7.5 1/10 M tris-(hydroxymethyl)-aminomethane-HCl buffer, and 1 ml ethylenediaminetetraacetic acid sodium salt aqueous solution). This is followed by subsequent bioautography with *Comamonas terrigena* B-996 as the assay organism.

The microorganisms isolated from soil whose biological active product gives an inhibitory zone at the same migration distance (or the same Rf value) as that of antibiotic PS-5 are selected as candidates for antibiotic PS-5 productions. Selected candidate microorganisms are further examined to confirm the antibiotic PS-5 producing ability by additional paper and thin layer chromatography studies.

By using the above mentioned methods, a person who is skilled in the art can select other antibiotic PS-5 producers beside the strain Streptomyces sp. A271 previously described.

According to an embodiment of this invention the antibiotic PS-5 may be produced by inoculating spores of the mycelium of a microbial strain capable of producing said antibiotic such as Streptomyces sp. A271 into a nutrient medium and cultivating it aerobically.

As the nutrients are employable many kinds of nutrients usually utilized by Streptomycetes, for example, carbon source, nitrogen sources, inorganic salts and the like. Employable nutrients are, for instance, the carbon sources of carbohydrates such as glucose, glycerin, maltose, sucrose, molasses, dextrin, starch or the like and of oils or fats such as soybean oil, peanut oil, lard or the like; the nitrogen sources such as pepton, meat extract, soybean meal, cotton seed oil, dried yeast, corn steep liquor, yeast extract, skimmed milk casein, sodium nitrate, ammonium nitrate, ammonium sulfate, or the like; and inorganic salts such as dipotassium phosphate, sodium chloride, calcium carbonate, magnesium sulfate, or the like; and trace metals, for example, cobalt, manganese or the like may be added if necessary. In addition, employable are all nutrients which can be utilized by the organism to produce the antibiotic PS-5. To prevent foaming during the heating sterilization and the fermentation, anti-foaming agents such as silicon oil, vegetable oil, or the like may be added.

Nutrients ratio in the formulation is not limited by the above description but can be changed within a broad range.

The most suitable nutrient formulation and composition can easily be determined by simple small scale experiments done by a person who is skilled in the art.

The medium may be sterilized prior to the cultivation.

The pH of the medium is preferably adjusted in the range from 4 to 9, preferably in the range from 6 to 8 before or after the sterilization.

Cultivation of the antibiotic PS-5 producing strain can be carried out essentially by a method similar to that which has been employed in general antibiotic production of antibiotics produced by Streptomycetes. Cultivation under aerobic conditions that is, cultivation under stirring and/or aeration is generally preferable.

Although any culture method among stationary culture, shaking culture and submerged culture is employable, submerged culture is the most preferable. Employable fermentation termperature is not particularly limited but it is generally selected within the range in which the growth of antibiotic PS-5 producer is not substantially inhibited and can produce the antibiotic PS-5. Although the fermentation temperature may be changed with the kind of procuding strain used, in general, suitable temperature is in the range of 20° to 40° C., preferably 25° to 35° C.

The pH of culture broth may be adjusted during fermentation in the range of 4 to 9, preferably of 6 to 8.

In large scale fermentation, it is preferable to cultivate an adequate seed culture and then to inoculate the nutrient medium for the submerged culture with said seed culture.

The fermentation may be usually continued until a sufficient amount of the antibiotic PS-5 is accumulated. The fermentation time is usually in the range of 30 to 90 hours but it varies with the medium composition, the fermentation temperature, the producing strain used and the like.

The optimal fermentation conditions to be used can be easily determined after small experiments conducted by a person who is skilled in the art. The accumulated amount of the antibiotic PS-5 in the fermentation broth can be determined by the bioassay method and bioautography which are described further on.

As the accumulated antibiotic PS-5 in the fermented materials is water soluble and is located mainly out of mycelium, it is preferable to remove the mycelium after fermentation by commonly known separation process such as filtration, centrifugation, extraction of the like, and to recover the antibiotic from the filtrate, supernatant, extract or the like.

Recovery of the antibiotic may be conducted by various processes commonly known. In particular, a preferred method to be applied for recovering the antibiotic is the method which has been frequently employed for recovering carboxylic acid type antibiotics.

For example, the following procedures can be employed independently or in combination or repeatedly for the recovery and the isolation of the antibiotic PS-5: (a) extraction at low pH with a solvent such as ethyl acetate, n-butanol, or the like, and back extraction from the solvent layer into an aqueous layer at higher pH; (b) extraction at neutral pH with solvents such as methylene chloride, chloroform, or the like, in the presence of a lipophilic quaternary ammonium salt such as benzalkonium chloride, tetra n-butyl ammonium hydrogen sulfate, or the like, or a crown compound such as the dicyclohexyl-18-crown-6, and 15-crown-5 NISSO crown ethers (Nippon Soda Co., Ltd.) and back extraction from the solvent layer into neutral aqueous layer containing sodium iodide, potassium iodide or the like; (c) adsorption on activated carbon, or high porous styrene/divinylbenzene resins such as Amberlite XAD (Rohm & Haas Co.), Diaion HP-20 (Mitsubishi Chemical Industries Ltd.) or the like and elution with aqueous methanol, aqueous acetone or the like; (d) adsorption and elution with ion exchange resin such as Dowex 1-X2 (Dow Chemical Co.) QAE-Sephadex A-25 (Pharmacia Fine Chemicals AB) or the like; (e) gel filtration with Sephadex G-10 (Pharmacia Fine Chemicals AB), Bio-Gel P-2 (Bio-Rad Loboratories), Bio-Beads S-X3 (Bio-Rad Laboratories) or the like; (f) column or thin layer chromatography with cellulose, Avicel SF (American Viscose Corp.), DEAE-Cellulose Whatman DE-32 (Whatman Ltd.), DEAE-Sephadex A-25 (Pharmacia Fine Chemicals AB), silica gel, alumina, or the like; and (g) forced precipitation by adding solvent such as acetone, etc. The behavior of the antibiotic PS-5 in the recovery and isolation processes can be recognized by determining the antibiotic PS-5 by a bioassay method and bioautography which are described later. In the above indicated manner, one can obtain the antibiotic PS-5 showing the characteristics described in the following.

Physico-chemical properties of antibiotic PS-5

(1) Solubility

The antibiotic PS-5 is soluble in water at pH 6 to 9. More specifically, this antibiotic is soluble not only in water at pH 7 but also in a slightly acidic aqueous medium adjusted to pH 6 or a higher than 6 by adding, for example, hydrochloric acid, etc., and in a weakly alkaline aqueous medium adjusted to a pH lower than 9 by adding, for example, sodium hydrogen carbonate, sodium hydroxide, etc.

This antibiotic is substantially insoluble in ethyl acetate and benzene at pH above 4.

(2) Thin layer chromatography (TLC)

The antibiotic PS-5 (sodium salt) gives the following Rf values when tested with the following TLC plates and solvents. The solvent ratios of the mixture of solvents employed are expressed as volume to volume ratio unless otherwise specified.

| | |
|---|---|
| (a) Avicel ® SF cellulose thin layer plate (Funakoshi Pharmaceutical Co., Ltd) | |
| n-Butanol/ethanol/water(7/7/6) | Rf = 0.94 |
| i-Propanol/water(7/3) | Rf = 0.96 |
| (b) Pre-coated silicagel plates 60 $F_{254}$ (E. Merck) | |
| Ethanol/water (7/3) | Rf = 0.82 |
| n-Propanol/water (7/3) | Rf = 0.77 |

(3) Paper chromatography

The antibiotic PS-5 (sodium salt) gives the following Rf values, when the Toyo Filter Paper No. 50 (Toyo Roshi Kaisha Ltd.) is employed and descending paper chromatography is developed with the following solvents:

| | |
|---|---|
| n-Propanol/water (7/3) | Rf = 0.68 |
| n-Propanol/i-propanol/water(7/7/6) | Rf = 0.70 |
| Acetonitrile/water (8/2) | Rf = 0.36 |
| Acetonitrile/Tris/EDTA (Note 1) | Rf = 0.34 |
| Ethanol/water (7/3) | Rf = 0.63 |

Note 1:
Mixed solvent composed of 120 ml acetonitrile, 30 ml pH 7.5 1/10 M tris-(hydroxymethyl)-aminomethane-hydrochloric acid buffer and 1 ml pH 7.5 1/10 M ethylenediamine tetraacetic acid sodium salt.

(4) High voltage paper electrophoresis

The following behavior is observed when the antibiotic PS-5 (sodium salt) is subjected to electrophoresis on Toyo Filter Paper No. 50 (Toyo Roshi Kaisha Ltd.) by using high voltage paper electrophoresis apparatus (Savant Instruments Inc., High Voltage Power Supply HV 3000A, Flat Plate Electrophoresis Chamber FP18A): at least 5 mm, usually 10;14 40 mm migration to the anode by charging for 30 min on a potential gradient of 42 volts per cm in pH 8.6 buffer composed of 3000 ml water, 3.3 g barbital and 25.5 g barbital sodium.

(5) Acidity

Antibiotic PS-5 is a mono basic acid having one carboxylic acid in the molecule.

(6) UV absorption spectrum

Characteristics UV absorption maximum of antibiotic PS-5 (sodium salt) is as follows:
$\lambda_{max}^{H2O} = 301$ nm

(7) IR absorption spectrum

Characteristic IR absorption maxima of the antibiotic PS-5 (sodium salt) measured by KBr tablet method are as follows:

| | |
|---|---|
| Approximately 1750 cm-1 | (—CO— in β-lactam ring) |
| approximately 1650 cm-1 | (—CO— of amide) |
| approximately 1640-1540 cm-1 | (—COO<sup>⊖</sup>) |

(8) Proton NMR spectrum

The antibiotic PS-5 (sodium salt) gives the following characteristic signals in 100 Mhz proton NMR spectrum measured in $D_2O$
(i) a triplet centred approximately at 1.06 ppm with coupling constants of approximately 7.5 HZ (C$\underline{H}_3$—CH$_2$—)
(ii) a multiplet approximately at 1.72–2.00 ppm (CH$_3$-C$\underline{H}_2$-)
(iii) a sharp singlet approximately at 2.05 ppm (C$\underline{H}_3$—CO—)
(iv) a multiplet approximately at 2.88–3.58 ppm (CH$_2$,

—CH—)

(v) a multiplet approximately at 3.92–4.20 ppm $$\underset{|}{N} \\ (-CH-)$$

(9) Specific rotation $[\alpha]_D^{22}$ +73.3 (C, 1.59, 0.01 M pH 8 Sodium phosphate buffer)

(10) Molecular weight and molecular formula

The molecular weight is approximately 298 (calculated from the results of the high resolution mass spectrometry for the methyl ester of the antibiotic PS-5). The molecular formula is:

$C_{13}H_{18}N_2O_4S$

(11) Color reaction

| | |
|---|---|
| Ehrlich reagent reaction: | positive |
| Iodine-chloroplatinic acid reaction: | positive |
| Ninhydrin reaction: | negative |

By the above physico-chemical properties, it is definitely demonstrated that the groups CH$_3$—CH$_2$—, CH$_3$CO—, —CH$_2$—,

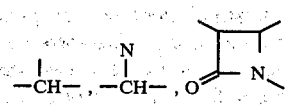

—NHCO—, and COO<sup>⊖</sup> are present in a molecule of the antibiotic PS-5 (sodium salt).

Elementary analysis of the trityl ester of antibiotic PS-5 (Example 10) reveals the presence of sulfur. The data of UV absorption maximum and minimum as well as their absorbancy ratio and extinction coefficient, give support to the presence of thienamycin skeleton in the molecule. This is confirmed by the fact that the UV absorption maximum is shifted from 301 nm to 315 nm by esterification of carboxyl moiety (16th Interscience Conference on Antimicrobial Agents % Chemotherapy, Chicago, Oct. 29, 1976). On the basis of the above evidences, antibiotic PS-5 is believed to have a molecular structure as follows:

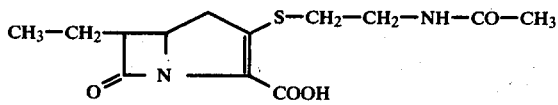
(I)

This is supported by the additional evidences that, as described later on (Example 9), the antibiotic PS-5 gives 13 signals in $^{13}$C-NMR spectrum and their chemical shifts are consistent with the above structure in comparison with data of thienamycin.

Though the antibiotic PS-5 appears to be unstable when, for example, the isolation is carried out at room temperature, it is fairly stable at low temperature, for example, below 0° C., particularly below −10° C. It is fairly stable in aqueous solution at around neutral and weakly alkaline pH. At least 50%, and usually more than 70% of the antibiotic activity of the antibiotic PS-5 remains after at least 15 min of heating at 60° C. in an aqueous solution at between around neutral and a weakly alkaline pH below pH 9.

Biological properties of the antibiotic PS-5

(1) Antibiotic spectra

The antibiotic PS-5 of this invention, having broad spectrum antibiotic activity, shows very strong antivity against various bacteria, for example, Gram-positive bacteria belonging to genera such as Staphylococcus, Diplococcus, Streptococcus, Sarcina, Bacillus and the like, and Gram-negative bacteria belonging to genera such as Alcaligenes, Comamonas, and the like. The antibiotic PS-5 of this invention also shows good activity against Gram-negative bacteria belonging to genera such as Escherichia, Klebsiella, Proteus, and the like.

The antibiotic PS-5 shows strong activity against Gram-negative bacteria which are resistant to the antbiotics having β-lactam ring structure, for example, those bacteria belonging to the genera such as Citrobacter, Proteus, Enterobacter, Klebsiella, Serratia, and the like.

(2) Increasing antibiotic activity of other antibiotics against β-lactamase-producing bacteria The antbiotic PS-5 of this invention has the ability to increase the antibiotic activity of other antibiotics, especially of β-lactam antibiotics such as penicillins and cephalosporins, against β-lactamase-producing bacteria such as Citrobacter freundii, Proteus vulgaris, Enterobacter aerogenes, Serratia marcescens, and the like. The activity patter is synergistic in most cases.

(3) Activity in vivo

The antibiotic PS-5 when administered to mice infected with pathogenic Gram-positive bacteria, shows a marked therapeutic effect.

(4) Toxicity

The antibiotic PS-5 does not provoke any dead in the test animals when administered intraperitoneally to mice at a dose of 500 mg/kg.

Derivatives of Antibiotic PS-5

Since the antibiotic PS-5 is somewhat labile as above described, the recovery and isolation processes must be conducted with great care. Since the antibiotic PS-5 is in general more stable in the salt form than in the free acid state, tha salt form is preferable when employed for pharmaceutical use and when employed as an intermediate material for synthesizing the derivatives, and during the isolation procedure. The salt form above described includes, for example, the following: alkali metal salts such as sodium salt, potassium salt, lithium salt or the like; alkaline earth metals salts such as calcium salt, magnesium salt or the like; other metal salts such as aluminum salt or the like; ammonium salt; salts with primary, secondary or tertiary amine such as monoethylamine, dimethylamine, triethylamine, monoethanolamine, diethanolamine or the like; and salts with organic base such as benzathine, procaine or the like. Suitable salts are pharmaceutically acceptable salts i.e. salts with cations which do not unfavorably affect the pharmacological and toxicological properties of the free acid. Particularly suitable salts are alkali metal salts such as sodium, potassium or the like.

As described above, antibiotic PS-5 of this invention is a monobasic acid having a carboxylic group in the molecule. It is therefore, apparent that various esters can be derived from the antibiotic with various alcohols, mercaptanes or derivatives thereof to produce esters, in the same manner as those of the known antibiotics clavulanic acid or thienamycin, for example. Therefore, the invention covers also these esters.

According to this invention a suitable ester of antibiotic PS-5 is an ester having the following general formula

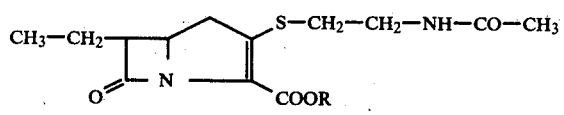
(II)

wherein R indicates a lower alkyl group or a triphenylmethyl group. In the above formula (II), the lower alkyl group identifies a straight chain or branched chain group, in particular, an alkyl groups having less than six carbon atoms, and more particularly a group having 1 to 4 carbon atoms. The examples are methyl, ethyl, n-propyl, isopropyl, n-butyl, isobutyl, n-pentyl, isopentyl, n-hexyl and the like. According to this invention, esters of the above formula (II) can be produced by reacting the antibiotic PS-5 of formula (I) or the salts thereof with the compounds of general formula (III)

RY (III)

wherein, R has the same meaning of the above and Y indicates an atom or group that can be cleaved off, or with lower diazoalkanes.

As to the atoms or groups Y in the general formula (III), employable are any kind of atoms or groups which can be cleaved off when brought into contact with the carboxyl group of the antibiotic PS-5, for example, halogen atoms such as chlorine, bromine, or iodine, sulfonyloxy groups; reactive carbonyloxy groups such as —O—CO—CF₃; and the like. The halogen atoms are particularly preferred.

Representative examples of the compound of the said general formula (III) are as follows:

Methyl alcohol, methyl iodide, dimethyl sulfate, methyl mercaptane, ethanol, ethyl bromide, ethyl iodide, ethyl mercaptane, n-propyl chloride, n-propyl iodide, propyl alcohol, isopropyl alcohol, isopropyl bromide, n-butyl alcohol, n-butyl bromide, n-butyl iodide, n-pentyl alcohol, n-pentyl chloride, n-pentyl bromide, n-pentyl iodide, n-hexyl alcohol, n-hexyl bromide, n-hexyl iodide, trityl alcohol, trityl mercaptane, trityl chloride, trityl bromide and the like.

One of the representative examples of the lower diazoalkanes suitable for producing the esters of the antibiotic PS-5, is diazomethane.

The reaction of the antibiotic PS-5 with the compounds of general formula (III) or with the lower diazoalkanes can be carried out by known methods for esterification. For example, the reaction of the antibiotic PS-5 with the compounds of general formula (III) or with the lower diazoalkanes is preferably carried out in an inert liquid medium, although it can be carried out also in the absence of said medium. The employable inert medium is for example selected from:(a) hydrocarbons such as benzene, toluene, n-hexane, cyclohexane or the like, (b) halo-hydrocarbons such as chloroform, methylene chloride or the like, (c) amides such as dimethyl formamide, hexamethyl-phosphotriamide or the like, (d) dimethylsulfoxide,(e) ether such as diethyl ether, diisopropyl ether, di n-butyl ether, tetrahydrofuran, dioxan or the like, (f) ester such as ethyl acetate, n-butyl acetate or the like, and (g) ketone such as acetone, methyl ethyl ketone or the like. These solvents can be used singly or as a mixture of two or more of them.

The reaction temperature is not critical and can be changed broadly with the type of the compounds of general formula (III), the type of the lower diazoalkane, the type of liquid medium or the like which is employed. The reaction temperature can be selected in the range in which the antibiotic PS-5 is not markedly decomposed but, in general, a suitable temperature is below 60° C., preferably in the range between 0° and 40° C., and more preferably in the range between 5° C. and the room temperature. In carrying out said reaction, a reaction stimulator such as trimethylamine, triethylamine, pyridine, dicyclohexylcarbodiimide or the like may be added, if necessary. Under these conditions, the reaction can be completed within 1-24 hours, usually 3-12 hours.

According to a preferred embodiment the invention, the antibiotic PS-5 employed for the reaction with the reactive derivative of formula III wherein R is triphenylmethyl, is not necessarily an isolated purified preparation. Even the cultured material or the filtered broth after removing mycelia from the cultured material can be employed for the reaction as well as the crude preparation of antibiotic PS-5 which has been partially purified by the recovery and isolation processes above described. Example of the partially purified preparation are: (a) a concentrated eluate from activated carbon with which the filtered broth has been treated; (b) a concentrated eluate from a styrene/divinylbenzene resin such as Diaion HP-20 (Mitsubishi Chemical Industries Ltd.) to which the filtered broth has been subjected; (c) a desalted concentrate with activated carbon of an eluate obtained with a gradient concentration of sodium chloride in phosphate buffer from an ion exchange resin such as for instance QAE-Sephadex (Pharmacia Fine Chemicals) on which the above mentioned concentrated eluate from Diaion HP-20 has been adsorbed; (d) a concentrated methylene chloride extract in the presence of benzalkonium chloride; (e) a concentrated extract with chloroform in the presence of crown compounds; and (f) a concentrated butanol extract at pH 3.5 at low temperature.

The antibiotic PS-5 trityl ester thus formed can be isolated from the reaction mixture and purified by various known methods. For example, after the reaction has been completed, the reaction mixture is at first poured into an aqueous medium to remove the aqueous impurities such as the byproducts or the like. It is preferred to use a neutral buffer as the aqueous medium to keep the pH close to the neutrality. The antibiotic PS-5 trityl ester in this mixture is then extracted with a less polar organic solvent not substantially miscible with water such as ethyl acetate, benzene, chloroform of the like. During the extraction step, a salt such as sodium chloride, ammonium sulfate or the like may be added to enhance the extraction efficiency.

After drying the organic extract over anhydrous sodium sulfate, the trityl ester can be isolated from the solvent layer by known methods, such as for example, gel filtration using Bio-Beads S-X3 (Bio-Rad Laboratories), Sephadex LH-20 (Pharmacia Fine Chemicals AB), or the like; or adsorption chromatography using a carrier such as silica gel, alumina, fuller's earth (Floridin Co.) or the like, which can be used in some adequate combination and used repeatedly, if necessary.

The trityl ester can be further purified by crystallization from a solvent or a mixture of solvents such as benzene, toluene, xylene, ethyl acetate, diethyl ether, methylene chloride, chloroform, hexane, petroleum ether (boiling in the range between 30° and 60° C.) or the like.

Among the esters of general formula (II) which can be produced by the above processes, the antibiotic PS-5 trityl ester having formula (II-a)

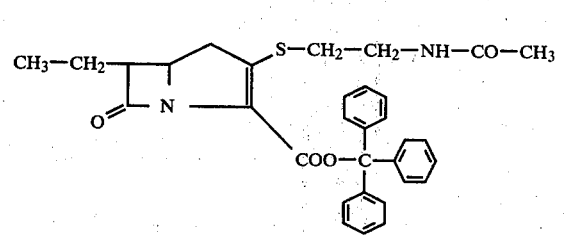

(II-a)

is characterized as one of the most useful esters by the following properties: it is more stable in comparison with the antibiotic PS-5 of formula (I) so that it makes isolation earier and it preserves a strong antibiotic and β-lactamase inhibitory activities, whereas the trityl ester of known penicillins, for example, do not show any substantial antibiotic activity. Furthermore, said trityl ester of formula (II-a) is very important as one of active esters and useful intermediates for the synthesis of other pharmaceutically useful products since the trityl group may be easily cleaved off.

Physico-chemical and biological properties of the trityl ester of antibiotic PS-5 this invention are given in detail in the following.

Physico-chemical properties of the antibiotic PS-5 trityl ester

A) Melting point

The trityl ester melts between 83° and 88° C.

The melting point in this case is measured by the Kofler method with the temperature raising rate of 1° C. per minute (apparatus:

The melting point test apparatus type BY-1, Yazawa Scientific Mfg. Co. Ltd.).

(B) Ultraviolet absorption spectrum $\lambda_{max}^{CH_3OH} = 315.5$ nm

(C) Infrared absorption spectrum

The most characteristic absorption maxima in chloroform solution, occur at the following wave numbers: 3430, 3100-3000, 2990, 2950, 1770, 1695, 1665, 1445, 1340, 1275 and 1139 cm$^{-1}$.

(D) Solubility

It is substantially insoluble in water, hexane and petroleum ether (boiling point: 30°-60° C.); soluble in benzene, ethyl acetate, chloroform, acetone, and dimethyl sulfoxide.

(E) Color reaction

| | |
|---|---|
| Ehrlich reagent reaction | positive |
| Triphenyltetrazolium chloride reaction | negative |
| Ferric chloride reaction | negative |
| Iodine-chloroplatinic acid reaction | positive |
| Hydroxylamine-ferric chloride reaction | positive |
| Chlorine-tolidine reagent reaction | positive |
| Ninhydrin reaction | negative |

(F) Color of the substance: colorless

(G) Thin layer chromatography (TLC)

The Rf values on the plates and with the solvents indicated below are as follows:

| | |
|---|---|
| (a) "Chromagram Sheet No. 6065" (Eastman Kodak Co.) | |
| Upper layer of n-Butanol/Ethanol/Water (4/1/5) | Rf = 0.56 |
| i-Propanol/Water (8/7) | Rf = 0.91 |
| n-Butanol | Rf = 1.0 |
| i-Propanol/water (1/4) | Rf = 1.0 |
| (b) Pre-coated silicagel plates 60 F$_{254}$ (E. Merck) Benzene/Acetone (2/1) | Rf = 0.29 |

(H) Proton nuclear magnetic resonance spectrum

The NMR spectrum at 100 MHz of the trityl ester in CDCl$_3$ reveals the following characteristic signals:
(i) a triplet centred approximately at 1.10 ppm with coupling constants of approximately 7.0 Hz.
(ii) a singlet near 1.86 ppm
(iii) a multiplet at approximately 7.0 to 7.67 ppm The above physico-chemical properties are consistent with the structure (II-a).

In particular, the following facts definitely confirm that the tritylation product of the antibiotic PS-5 is an ester.
(i) a broad IR absorption of —COO$^\ominus$ at approximately 1640-1540 cm$^{-1}$ which is shown in IR spectrum of the antibiotic PS-5 (sodium salt) is not observed in IR spectrum of the trityl ester thereof.

Instead, the trityl ester gives a sharp absorption of a group —CO— in an ester moiety at approximately 1695 cm$^{-1}$.
(ii) the antibiotic PS-5 cannot substantially be extracted with solvent from neutral or weakly alkaline aqueous solution, but the trityl ester can be easily extracted.
(iii) The UV absorption maximum of the antibiotic PS-5 is 301 nm, while that of the trityl ester is 315.5 nm. This shifting is analogous to the case of N-acetyl-thienamycin methyl ester.

Biological properties of the antibiotic PS-5 trityl ester

(1) Antibiotic spectra

The trityl ester of the antibiotic PS-5 has broad spectrum antibiotic activity and in particular shows a very strong activity against various Gram-positive bacteria belonging to genera such as Staphylococcus, Diplococcus, Streptococcus, Sarcina, Bacillus and the like and Gram-negative bacteria belonging to genera such as Alcaligenes, Comamonas, and the like.

The trityl ester of antibiotic PS-5 also shows good activity against, Gram-negative bacteria belonging to genera such as Escherichia, Klebsiella, Proteus, and the like.

A remarkable characteristic shown by the trityl ester of the antibiotic PS-5 is its strong activity against Gram-negative bacteria which are resistant to the antibiotics having β-lactam ring structure and belong, for example, to the genera Citrobacter, Proteus, Enterobacter, Klebsiella, Serratia, and the like.

(2) Increase of antibiotic activity of other antibiotics against β-lactamase producing bacteria The trityl ester of the antibiotics PS-5 has also the ability to enhance the antibiotic activity of other antibiotics, especially of β-lactam antibiotics such as penicillins and cephalosporins, against β-lactamase producing bacteria such as *Citrobacter freundii*, *Proteus vulgaris*, *Enterobacter aerogenes*, *Serratia marcescens*, and the like.

(3) Activity in vivo

The trityl ester of the antibiotic PS-5 when administered to mice infected with a pathogenic Gram-positive bacteria, shows a marked therapeutic effect.

(4) Toxicity

The trityl ester does not provoke any dead in the test animals when administered intraperitoneally to mice at a dose of 500 mg/kg.

Method of use and pharmaceutical preparations of the antibiotics PS-5 and its derivatives The antibiotic PS-5 and the derivatives thereof described before may be represented by the following general formula (A)

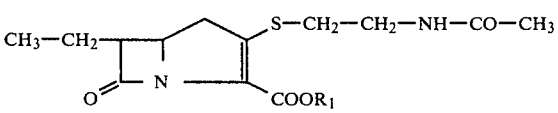

wherein $R_1$ represents hydrogen, lower alkyl and triphenylmethyl and including the salts of the compound wherein $R_1$ is hydrogen.

In the above general formula the term "lower alkyl" is defined in the same way as above for the symbol R of the formula II representing the esters of the antibiotic PS-5. The expression "the salts of the compound wherein $R_1$ is hydrogen" identifies the salts of the antibiotic PS-5 as defined before under the paragraph illustrating the derivatives of the antibiotic PS-5, and obviously includes also the pharmaceutically acceptable salts of said antibiotic.

Antibiotic PS-5 and its derivatives, particularly the trityl ester, exhibit in vitro and in vivo activity against Gram-negative and Gram-positive microorganisms and therefore are useful in controlling and preventing bacterial infections in test animals.

The antibiotic PS-5 or its trityl ester and compositions may be administered orally, topically or parenterally (intraveneously, intramuscularly, intraperitoneally, etc.) and may be used in a variety of usual pharmaceutical preparations depending on the method of administration. For example, the antibiotic PS-5 or its trityl ester may be compounded with a pharmacologically acceptable carrier, diluent or the like in solid forms (for example, tablets, capsules, powders, granules, sugar-coated tablet, troches, powder sprays, suppositories, etc), semi-solid forms (for example, ointments, creams, semi-solid capsules, etc.), or liquid forms (for example, liquid solutions, emulsions, suspensions, lotions, syrups, solution for injection, liquid sprays, etc.).

The unit dose preparation containing the antibiotic PS-5 or the trityl ester thereof may contain generally from 0.1 to 99 weight % of the active component in any form of liquid, semi-solid and solid form.

Representative additives of carriers, fillers, diluents, or the like which can be used for these preparations and also method of preparation are further described in the following.

Tablets and capsules for oral administration may be in unit dose preparation form and may contain binding agents, for example, syrup, acacia, gelatin, sorbitol, tragacanth, polyvinylpyrrolidone or the like; fillers, for example, lactose, sucrose, starch, calcium phosphate, sorbitol, glycine or the like; lubricants, for example, magnesium stearate. talc, polyethylene glycol, silica or the like; disintegrants, for example, potato starch or the like; or wetting agents such as sodium lauryl sulfate or the like. The tablets may be coated according to methods well known in the art.

Liquid preparations for oral uses may be in the form of oily or aqueous suspensions, solutions, emulsions, syrups, etc., or may be provided as dry products that can be confirmed with water or other suitable vehicles before use. The said liquid preparations for oral uses may contain the following pharmaceutically permissible ingredients: suspending agents (for example, methyl cellulose, sorbitol syrup, sugar syrup, hydroxyethyl cellulose, gelatin, carboxymethyl cellulose, aluminium stearate gel, hydrogenated edible fats and oils); emuslifying agents (for example, acacian lecithin, sorbitan monooleate); non-aqueous vehicles (for example, ethyl alcohol, propylene glycol, oily esters, fractionated coconut oil, almond oil); preservatives (for example, methyl p-hydroxybenzoate, propyl p-hydroxybenzoate, sorbic acid).

Suppositories may contain conventional suppository bases like cocoa butter and various glycerides.

Compositions for injection may be prepared in unit dose form in ampules or in multidose containers with a preservative. They may be in the form of suspensions, solutions and emulsions in oily or aqueous vehicles, and if necessary, may contain formulatory agents such as suspending agents, dispersing agents and stabilizing agents. Alternatively, the antibiotic of the present invention may be prepared in the powder form which can be combined with pyrogen-free, sterile water before use.

Compositions containing the antibiotic PS-5 and or its trityl ester may be provided in various forms suitable for absorption through the mucous membrane of the nose, throat and bronchial tube. For example, the form of powder or liquid sprays, inhalants, troches, throat paints, etc. will be advantageous for the said purposes. For treatment of the ears and eyes, the antibiotic of the present invention may be prepared as individual capsules, as drops, in liquid or semi-solid form, etc. In addition, for topical applications it may be presented as formulations in hydrophilic or hydrophobic bases such as powders, lotions, creams, ointments, and the like.

If desired, in addition to a carrier, the compositions described above may contain other ingredients, for example, preservatives, antioxidants, lubricants, viscosity agents, flavoring agents, suspending agents, binders, stabilizing agents, and the like.

When the antibiotic PS-5 and/or its trityl ester are intended for uses such as treatment of infections in pigs, cows, sheep, chickens and the like, the formulations may be presented as intramammary preparations in long-acting or quick-releasing bases, for instance, or as feed additive concentrates. The above described pharmaceutical compositions according to the present invention may contain antibiotic PS-5 and/or its trityl ester as the sole active ingredient or in combination with other therapeutically effective ingredients.

As explained above in detail, because the antibiotic PS-5 and its trityl ester have a synergistic effect on various $\beta$-lactamase producing bacteria in combination with $\beta$-lactam compounds, it will be advantageous to combine them with $\beta$-lactam compounds in pharmaceutical compositions.

As a suitable example of beta-lactam compounds can be mentioned penicillin derivatives such as benzylpenicillin, phenoxymethylpenicillin, carbenicillin, ampicillin, and amoxicillin; and cephalosporin derivatives such as cephaloridine, cephalotin, cefazolin, cephalexin, cefoxitin, cephacetrile, cephamandole, cephapirin, cephradine and cephaloglycin.

When antibiotic PS-5 and/or its trityl ester are (is) combined with one or more members of the above listed beta-lactam compounds, the combining ratio of the antibiotic of this invention to the known beta-lactam compound(s) is not critical, but may vary in a wide range. But, from the practical viewpoint, it will be advisable to use the quantitative ratio of the antibiotic of this inventions to the known beta-lactam compound(s) in the range of 20:1 to 1:150, and preferably 10:1 to 1:100.

In the treatment of bacterial infections in mammals, the dose of antibiotic PS-5 and/or its trityl ester can be varied depending on the subject of the treated, the body weight, the type, severity and symptom of infections, the mode and number of administration, etc. For usual oral or parenteral administration, it will be profitable to use the daily dose in the range of 0.05 mg/kg, to 500 mg/kg, preferably 0.5 mg/kg, to 200 mg/kg more preferably in a divided dosage. It is clear that a dose beyond the above recommended range, may also be employed depending on the individual conditions of the subject to be treated.

The antibiotic PS-5 and/or its trityl ester not only can be used in pharmaceutical compositions as explained above but also may be added directly or as feed additive concentrates in animal feeds. In addition, they may be utilized as the active ingredients for food preservatives or disinfectants.

DESCRIPTION OF SOME PREFERRED AMBODIMENTS

The following Examples will illustrate the present invention. In all Examples, the quantitative and qualitative assays of antimicrobial activity were based on the following methods:

(1) Bio-assay of antimicrobial activity

The overnight culture of *Comamonas terrigena* B-996 on a nutrient agar slant was suspended in nutrient broth so as to give an optical cell density of 0.040 at 610 nm.

The seed suspension was added in a 1% amount to a molten agar medium containing 0.8% Kyokuto Nutrient Broth Powder (Kyokuto Pharmaceutical Industries Co.) and 1.0% Bacto-Agar (Difco Laboratories). Seven milliliters of the seeded molten agar medium were distributed in a Petri dish (9 cm in diameter) and solidified). This is defined as a Comamonas assay plate.

*Staphylococcus aureus* FDA 209P was cultivated overnight in nutrient broth with shaking and diluted 50 fold in nutrient broth to provide the seed suspension. A 1% (v/v) amount of the seed suspension was mixed well with molten agar medium containing 1% Kyokuto Nutrient Broth Powder (Kyokuto Pharmaceutical Industries Co.) and 1% Bacto-Agar (Difco Laboratories). Seven milliliters each of the seeded molten agar medium was poured and gelled in a Petri dish (9 cm in diameter). This is defined as a Staphylococcus assay plate.

In a similar way, an Alcaligenes assay plate was prepared. The one night-old nutrient agar slant culture of *Alcaligenes faecalis* B-326 was suspended in nutrient broth to provide the seed suspension, the cell concentration of which was adjusted to an optical density of 0.020 at 610 nm. Agar medium composed of 0.5% Kyokuto Nutrient Broth Powder (Kyokuto Pharmaceutical Industries Co.) and 1.0% Bacto-Agar (Difco Laboratories) was melted at a permissible temperature and seeded with a 1.0% inoculum of the seed suspension. Seven milliliters of the seeded molten agar medium were distributed into a 9 cm Petri dish and allowed to gel. This is defined as an Alcaligenes assay plate.

An 8 mm pulp disc was usually soaked with a sample solution to be assayed, left on a clean sheet of filter paper for a sufficient time to remove the excess solution and then transferred onto an assay plate. After incubation at 35° C. for 20 hours, the diameter of the observed inhibition zone was measured and compared with standard solutions of cephaloridine. The antimicrobial activity of the antibiotic PS-5 and related compounds is expressed as cephaloridine equivalent units/ml.

More particularly, a solution of antibiotic PS-5 and related compounds of the present invention which shows the same diameter of inhibition zone as 100 μg/ml of cephaloridine is expressed as 100 cephaloridine units/ml. Similarly when a solid sample of antibiotic PS-5 and related compounds of this invention exhibits at a concentration of 1 mg/ml the same diameter as 1 μg/ml of cephaloridine, the specific activity of the solid sample is shown as 1 cephaloridine unit/mg. As well known to those skilled in the art, the assay standard curve varies to some extent, depending on the species of the test microorganisms. To specify the species of the test microorganisms, the following unit expression was employed: Comamonas-cephaloridine unit (abbreviated as CCU); Staphylococcus-cephaloridine unit (abbreviated as SCU); and Alcaligenes-cephaloridine unit (abbreviated as ACU).

(2) Bio-autography

A large assay plate was prepared as described in (1) above, except that 100 ml of the seeded molten agar medium was poured in a rectangular dish of 32×24 cm instead of a 9 cm Petri dish.

A paper chromatogram to be assayed was placed for 15 minutes on said large assay plate. After the paper was removed, the assay plate was incubated at 35° C. for 20 hours to reveal the inhibition zone(s). This technique permits not only to calculate the Rf value(s) (qualitative assay) but also to determine the antimicrobial activity (semi-quantitative assay) based on the size of the halo.

In case a TLC plate was employed, a sheet of thin paper was intercalated between the TLC plate and the surface of the assay plate. The similar procedure was carried out for qualitative and semi-quantitative assays.

DESCRIPTION OF THE DRAWINGS

FIG. 7 is the proton magnetic resonance spectrum of the said trityl ester of antibiotic PS-5.

EXAMPLE 1

Figure 1:
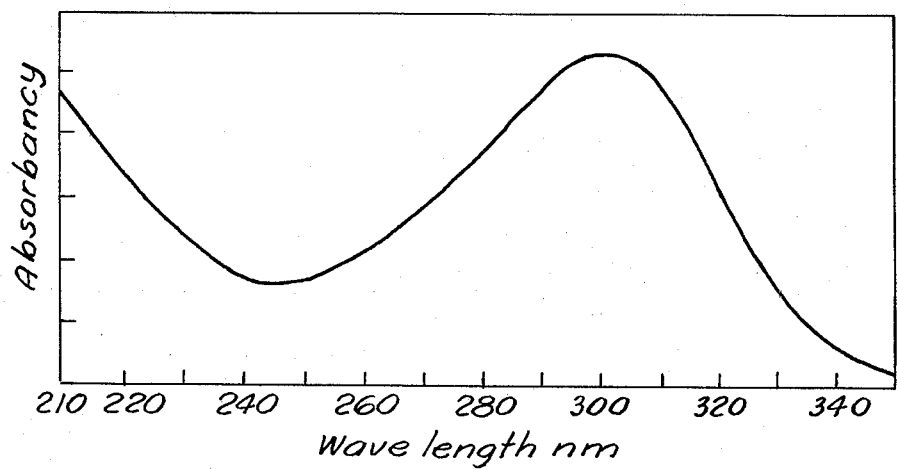
FIG. 1 is the ultraviolet absorption spectrum of the antibiotic PS-5 sodium salt prepared in Example 9 of this invention.

A 500 ml Erlenmeyer flask containing the following seed culture medium (SE-4) was sterilized at 120° C. for 15 minutes. To a well sporulated slant culture of Streptomyces sp. A271, 10 ml of 0.02% Tween-80 (a surfactant Atlas Powder Corp.) solution was added and the mixture was stirred slightly to produce the spore suspension. The 500 ml Erlenmeyer flask was inoculated with one milliliter of the spore suspension and shake-cultured at 28° C. for 48 hours on a rotary shaker (200 r.p.m.; radius of circle 3.5 cm). Then, 2 ml of the seed culture was inoculated into each of the six 500 ml Erlenmeyer flasks each containing 100 ml of the production media described below and shake-cultured at 28° C. for 48 to 96 hours on a rotary shaker.

SEED CULTURE MEDIUM (SE-4)

| | |
|---|---|
| Beef extract (Difco Laboratories) | 0.3% (w/v) |

-continued

| | |
|---|---|
| Bacto-tryptone (Difco Laboratories) | 0.5 |
| Glucose | 0.1 |
| Soluble starch | 2.4 |
| Yeast extract | 0.5 |
| Calcium carbonate | 0.4 |
| Defatted soybean meal | 0.5 | pH 7.5 prior to sterilization; pH 7.1 after sterilization; pH 7.4 after two days fermentation

PRODUCTION MEDIA (1) AG-1 medium

| | |
|---|---|
| Glucose | 1.5% (w/v) |
| Corn starch | 2.5 |
| Corn steep liquor | 2.0 |
| Dry yeast | 1.0 |
| D,L-methionine | 0.1 |
| $CoCl_2 \cdot 6H_2O$ | 0.00013 | pH 7.2 prior to sterilizaion; pH 6.1 after sterilization; pH 7.8 after four days fermentation (2) AGA-2 medium

| | |
|---|---|
| Glucose | 1.5% (w/v) |
| Potato Starch | 2.5 |
| Corn steep liquor | 2.0 |
| Dry yeast | 1.0 |
| $CoCl_2 \cdot 6H_2O$ | 0.00013 | pH 6.5 prior to sterilization; pH 5.8 after sterilization; pH 7.8 after four days fermentation (3) AGB-1 medium

| | |
|---|---|
| Maltose | 3.0% (w/v) |
| Corn steep liquor | 1.0 |
| Dry yeast | 1.0 |
| $CoCl_2 \cdot 6H_2O$ | 0.0001 | pH 6.5 prior to sterilization; pH 5.9 after sterilization; pH 7.9 after four days fermentation (4) AGB-41 medium

| | |
|---|---|
| Maltose | 5.0% (w/v) |
| Soluble starch | 1.0 |
| Glycerin | 0.3 |
| Dry yeast | 2.5 |
| NaCl | 0.5 |
| $K_2HPO_4$ | 0.05 |
| $MgSO_4 \cdot 7H_2O$ | 0.05 |
| $CaCO_3$ | 0.3 |
| $CoCl_2 \cdot 6H_2O$ | 0.00013 | pH 7.0 prior to sterilization; pH 6.9 after sterilization; pH 7.9 after four days fermentation (5) ML-19 medium

| | |
|---|---|
| Glycerin | 4.0% (w/v) |
| Peptone | 0.5 |
| Glucose | 0.2 |
| Potato Starch | 0.2 |
| Defatted soybean meal | 0.5 |
| Dry yeast | 0.5 |
| NaCl | 0.5 |
| $CaCO_3$ | 0.2 | pH 6.4 prior to sterilization; pH 7.0 after sterilization; pH 7.0 after four days fermentation (6) AGO-1 medium

| | |
|---|---|
| Soybean oil | 3.0% (w/v) |
| Dry yeast | 2.0 |
| NaCl | 0.5 |
| $K_2HPO_4$ | 0.05 |
| $MgSO_4 \cdot 7H_2O$ | 0.05 |
| $CaCO_3$ | 0.3 |
| $CoCl_2 \cdot 6H_2O$ | 0.00013 | pH 7.0 prior to sterilization; pH 7.2 after sterilization; pH 7.2 after four days fermentation The antibiotic potency of the broth filtrate was determined by the disc assay as described before, utilizing *Comamonas terrigena* B-996, *Staphylococcus aureus* 209P and *Alcaligenes faecalis* B-326. The results observed at 72 hours after inoculation are as follows:

TABLE 5

| Medium | Antibiotic potency | | |
|---|---|---|---|
| | CCU/ml | SCU/ml | ACU/ml |
| AG-1 | 105 | 1.1 | 420 |
| AGA-2 | 72 | 1.1 | 420 |
| AGB-1 | 105 | 0.9 | 340 |
| AGB-41 | 185 | 8.9 | 440 |
| ML-19 | 60 | 1.4 | 122 |
| AGO-1 | 67 | 0.9 | 340 |

EXAMPLE 2

One hundred milliliter of the seed culture prepared as described in Example 1 was transferred into a 30 liter jar fermentor containing 15 liter of ML-19 medium and cultivated under forced aeration at 28° C. for 96 hours at 200 r.p.m., the sterile air being fed at 7.5 liter/minute.

A silicon oil (Silicone KM-75, Shin-Etsu Chemical Industries Co., Ltd.) was employed as an anti-foamer at a concentration of 0.05%.

The fermentation broth was collected and centrifuged at the indicated times. The antibiotic potency of the broth filtrate was as follows:

TABLE 6

| Time | Potency (CCU/ml) | pH values |
|---|---|---|
| 24 hours | 19 | 7.0 |
| 48 | 48 | 7.2 |
| 72 | 72 | 7.1 |
| 96 | 59 | 7.0 |

EXAMPLE 3

Using a similar procedure as described in Example 1, *Streptomyces* sp. A271 was cultivated in a 500 ml Erlenmeyer flask containing 100 ml of SE-4 medium and then inoculated into a 30 liter jar fermentor containing 15 liter of SE-4 medium. After cultivation at 28° C. for 24 hours at 200 r.p.m. under the forced aeration of 7.5 liter/minute, one liter of the seed culture was poured in a 200 liter stainless steel tank fermentor containing 100 liter of ML-19 medium. The tank fermentor was aerated under agitation at 28° C. for 72 hours at 100 r.p.m., the aeration rate being maintained at 50 liter/minute. The initial pH was 7.0 while the final pH was 7.1. The broth was mixed with 5% (w/v) of perlite (Topco Perlite, Topco No. 34, Toko Perlite Kogyo K.K.) and filtered through a filter press to give 80 liter of broth filtrate. The antibiotic potency of the clear liquor was 60 CCU/ml.

EXAMPLE 4

PREPARATION OF THE ACTIVE CARBON CONCENTRATE

As described in Example 1, ten 500 ml Erlenmeyer flasks containing 100 ml each of ML-19 medium were incubated under shaking for 72 hours. To the combined broth, 2% (w/v) of perlite filter aid (Topco Perlite, Topco No. 34 Toko Perlite Kogyo K.K.) was added and filtered through a Buchner funnel to yield 800 ml of the broth filtrate. After the pH was confirmed to be in the range of 7-8, 16 g of active carbon (Charcoal Activated, Shirasagi; Takeda Chemical Industries, Ltd.) was added and stirred for 15 minutes. The active carbon was collected by centrifugation; washed with 800 ml of distilled water and then centrifuged. The active carbon thus recovered was eluted with 400 ml of 50% (v/v) acetone under stirring at room temperature for 30 minutes. The obtained supernatant solution (eluate) (52 CCU/ml) was concentrated to 50 ml at a temperature of 30°-35° C. in a rotary evaporator. The antibiotic titer of the concentrate was 800 CCU/ml.

The following experiments were carried out in order to clearly prove that antibiotic PS-5 of this invention is different from MM4550 (Complex) which is disclosed as beta-lactamase inhibitor in German Applns. DOS Nos. 2,513,855 and 2,513,854.

Three strains of *Streptomyces olivaceus* ATCC 31126 (=ATCC 21379/M3), ATCC 21380 and ATCC 21382 were cultured at 28° C. for 72 hours on a rotary shaker in a 500 ml Erlenmeyer flask containing 100 ml of the following medium:

| | |
|---|---|
| Soybean meal (ESSAN-M (Special grade); Ajinomoto Co., Ltd.) | 1.0 |
| Glucose | 2.0 |
| $CaCO_3$ | 0.2 |
| $CoCl_2 \cdot 6H_2O$ | 0.001 |
| pH 7.0 prior to autoclaving | |

The antibiotic activity in the filtered broth was adsorbed on active carbon, washed with water, and eluted with 50% acetone. The obtained eluate was concentrated to a small volume under reduced pressure and subjected to descending paper chromatography under the below indicated conditions:

| | |
|---|---|
| Filter paper: Toyo Filter Paper No. 50 (Toyo Roshi Kaisha, Ltd.) | |
| Solvent system: (80% Acetonitrile/Tris/EDTA system) | |
| acetonitrile | : 120 ml |
| M/10 tris(hydroxymethyl) aminomethane-HCl(pH 7.5) | : 30 ml |
| M/10 tetrasodium ethylenediamine-tetra-acetate(pH 7.5) | : 1 ml |

Rf values were revealed by bio-autography under the said conditions on *Comamonas terrigena* B-996.

In parallel with the above listed three strains of *Streptomyces olivaceus*, Streptomyces sp. A271 of the present invention was fermented in medium composed of glycerin 4.0%, glucose 0.2%, peptone 0.5%, potato starch 0.2%, defatted soybean meal 0.5%, dry yeast 0.5%, NaCl 0.5% and $CaCO_3$ 0.2% (pH 6.4 before autoclaving). The subsequent treatment and assay were the same as described above.

The bio-autographic tests proved that the antibiotic PS-5, a product of Streptomyces sp. A271 of the invention is a new product different from MM 4550 (Complex) disclosed in the above mentioned German applications.

EXAMPLE 5

PREPARATION OF THE CONCENTRATED DIAION HP20 ELUATE OF ANTIBIOTIC PS-5

As described in Example 1, 15 liters of ML-19 medium were fermented in 150 flasks for 72 hours. To the collected broth, 100 mg of disodium ethylenediaminetetraacetate and 2% (w/v) of Topco Perlite, Topco No. 34 were added and filtered through a large Buchner funnel to give 14.1 liter of the broth filtrate (pH 7.9). This was charged on a DIAION HP20 column 7×50 cm (a high porous styrene and divinylbenzene copolymer in a bead form having macroreticular structure and manufactured by Mitsubishi Chemical Industries, Ltd.), washed with 7 liters of distilled water and eluted with 50% (v/v) methanol. The elution pattern of the antibiotic activity was as follows (Table 7):

TABLE 7 charged activity: 40 CCU/ml × 14,000 ml

| Eluate No. | Volume (ml) | Potency (CCU/ml) |
|---|---|---|
| 1 | 1,000 | 0 |
| 2 | 500 | 0 |
| 3 | 500 | 0 |
| 4 | 50 | 19 |
| 5 | 50 | 37 |
| 6 | 50 | 72 |
| 7 | 50 | 150 |
| 8 | 50 | 270 |
| 9 | 50 | 850 |
| 10 | 50 | 870 |
| 11 | 50 | 300 |
| 12 | 50 | 270 |
| 13 | 50 | 230 |
| 14 | 50 | 200 |
| 15 | 50 | 170 |
| 16 | 50 | 125 |
| 17 | 50 | 105 |
| 18 | 50 | 87 |
| 19 | 50 | 75 |
| 20 | 50 | 60 |
| 21 | 50 | 48 |
| 22 | 50 | 38 |
| 23 | 50 | 27 |
| 24 | 50 | 18 |
| 25 | 50 | 14 |
| 26 | 50 | 10 |
| 27 | 50 | 0 |
| 28 | 50 | 0 |
| 29 | 50 | 0 |

Eluate Nos. 8 through 14 were combined, concentrated to 100 ml at a temperature below 30° C. in a rotary evaporator and then freeze-dried to provide 2.6 g of yellowish brown powder the potency of which was 54 CCU/mg.

Said yellowish brown powder was dissolved in distilled water at a concentration of 500 CCU/ml.

Phosphate buffer solutions of the indicated pH's were made by adjusting M/15 dipotassium phosphate to a desired pH with 5 N NaOH or 5 N phosphoric acid. To 1 milliliter of the antibiotic PS-5 solution, 1 milliliter of the phosphate buffer was added and, if necessary, the pH value was readjusted to the initial value. The antibiotic PS-5 solutions with varied pH's were kept at 60° C. for 30 minutes in a water bath, cooled in running water and neutralized to pH 7.0 with a small amount of 5 N NaOH or 5 N phosphoric acid. The control tube containing the antibiotic PS-5 solution of pH 7.0 was put in an ice bath for 30 minutes. The remaining antimicrobial activity was determined as described above, utilizing *Comamonas terrigena* B-996 as the assay microorganism. The results shown in the following table were calculated as percent of the control:

| pH | 3.0 | 4.0 | 5.0 | 6.0 | 7.0 | 8.0 | 9.0 |
|---|---|---|---|---|---|---|---|
| Remaining activity (%) | 0 | 0 | 9.0 | 79.0 | 76.5 | 88.5 | 82.0 |

These results show that the yellowish brown powder obtained in this Example is fairly stable at a pH in the range of 6.0 to 9.0 for 30 minutes at 60° C. In addition, the stability of antibiotic PS-5 seems to increase at a lower temperature even at an acidic pH. For example, after antibiotic PS-5 was treated at pH 3.0 for 5 minutes at $-17°$ C., at least 30% of the initial antibiotic activity was still detected.

EXAMPLE 6

EXTRACTION AT A LOW TEMPERATURE WITH n-BUTANOL

A large test tube containing 20 ml of distilled water, 12 ml of n-butanol and 7 g of sodium chloride was cooled down to $-17°$ C. without freezing. The yellowish brown powder of antibiotic PS-5 obtained in Example 5 was diluted at a concentration of 200 mg/ml in distilled water and pre-refrigerated. One milliliter of the cold solution of the antibiotic PS-5 was added to the said test tube and quickly adjusted to pH 2.75, pH 3.0 or pH 3.25 with sulfuric acid while the temperature of the mixture was maintained below a temperature of $-10°$ C. After thorough mixing, the n-butanol layer was recovered and mixed well with 5 ml of 0.5 M phosphate buffer (pH 6.8) whereby the active component was transferred into the aqueous layer. The bio-assay of the aqueous solution gave the following extractability of antibiotic PS-5 from the yellowish brown powder:

| pH | extraction percentage |
|---|---|
| 2.75 | 35% |
| 3.00 | 32 |
| 3.25 | 16 |

EXAMPLE 7

PREPARATION OF THE QAE-SEPHADEX POWDER

By the same procedure as described in Example 5, 27.7 g of the yellowish brown powder of antibiotic PS-5 were obtained from 100 liter of broth filtrate after freeze-drying. This powder (specific activity 13.2 CCU/mg) was dissolved in 30 ml of 25 mM phosphate buffer (pH 6.8) and applied on a column of QAE-Sephadex A-25 (a fully quaternized strongly basic anion exchange resin obtained by introduction of diethyl-2-hydroxypropyl ammonium groups into dextran gel; produced by Pharmacia Fine Chemicals AB) (3.3×25.0 cm) which had been equilibrated with the same buffer. After washing with a small amount of the same phosphate buffer, the activity was eluted with the same buffer containing sodium chloride, the concentration of sodium chloride being linearly changed from zero to 0.5 M during elution. The active fraction (300 ml) was cooled to $0°$ C. and treated with 6 g of active carbon. The active carbon was collected, washed with water and eluted with 50% (v/v) acetone. After acetone was removed by evaporation at a temperature below $30°$ C., 727 mg of brownish yellow powder of the antibiotic PS-5 sodium salt was recovered by lyophilization. The specific activity of this preparation was 264 CCU/mg.

EXAMPLE 8

PREPARATION OF THE DEAE-CELLULOSE POWDER

The brownish yellow powder (727 mg) of antibiotic PS-5 that was obtained in Example 7 was dissolved in 1 ml of 25 mM phoshate buffer (pH 6.8) and charged on a column (1.5×27.0 cm) of Bio-Gel P-2 (a gel beads cross-linked synthetic polymer composition based on methylene-bis-acrylamide copolymer; produced by BIO-RAD Laboratories) that had been equilibrated with the same phosphate buffer. By developing with the same phosphate buffer, the active fraction (15 ml) was obtained.

The obtained active fraction was then applied on a column (2.5×28.0 cm) of diethylaminoethyl (DEAE) cellulose DE32 (Whatman Ltd.) that had been equilibrated with the same phosphate buffer. The elution was carried out with a linear gradient of sodium chloride in the same phosphate buffer from 0 to 0.5 M. The recovered active fraction (240 ml) was adsorbed on 4.5 g of active carbon at a temperature of $0°$ C. The active carbon was collected by filtration, washed with water and eluted with 50% (v/v) acetone. The acetone eluate was evaporated below $30°$ C. until no acetone was detected, and then lyophilized to provide 120 mg of brownish white powder of antibiotic PS-5 sodium salt. The specific activity of this preparation was 600 CCU/mg.

EXAMPLE 9

HIGHLY PURIFIED PREPARATION OF ANTIBIOTIC PS-5

Two 200 liters stainless steel fermentation tanks were filled with 100 liter each of the ML-19 medium containing 2.5% defatted soybean meal, autoclaved, inoculated with Streptomyces sp. A271 in the same manners as described in Example 3, and fermented for 72 hours under aeration and agitation. The contents of the two fermentation tanks were combined, mixed with 5% (w/v) Topco Perlite, Topco No. 34 (Topco Perlite Kogyo K.K.) and filtered through a filter press to give 160 liter of the broth filtrate. The antibiotic titer of this filtrate was found to be 235 CCU/ml.

This broth filtrate was passed through an ion exchange resin column DIAION PA-306 (a strong base anion exchange resin having cross linked polystyrene matrix and trimethylammonium chloride moieties; produced by Mitsubishi Chemical Industries Ltd,; 10×52 cm; 4.5 liter in wet volume) without being retained. Then the activity passed through said column was adsorbed on a DIAION HP-20 column (14×97 cm; 15 liter) and eluted with 75% methanol. The collected active eluate (2 liters: 9,854 CCU/ml) was diluted three times with 4 liter of water and applied on a 2 liter column (5.5×84 cm) of DIAION PA-306S. After washing with 500 ml of water, the antibiotic activity was eluted with a 8 liter linear sodium chloride gradient from 0 to 3% and collected in 200 ml fractions. Active fractions from No. 17 to No. 31 were combined to make 2.8 liter of the active eluate (4,120 CCU/ml). This eluate was then charged on a 1-liter DIAION HP-20 column (4.5×63 cm) and eluted with a 3-liter linear gradient of acetone from 0 to 25%. The volume of each fraction was 30 ml. The active eluate (390 ml; 27,220 CCU/ml) was recovered by combining antimicrobially active fractions from No. 54 to No. 66.

After acetone was removed by distillation under reduced pressure, the DIAION HP-20 eluate was passed through a 200 ml column of QAE-Sephadex A-25 (2.5×41 cm). The antimicrobial activity was collected in 10 ml fractions by elution with a 2-liter linear sodium chloride gradient (0–1.5%). Fractions Nos. 68 to 81 were united as the active eluate (140 ml; 42,120 CCU/ml).

This QAE-Sephadex A-25 eluate was carefully adjusted to pH 8.3 with 1% of NaOH, and charged on a 200 ml DIAION HP-20AG (Mitsubishi Chemical Industries, Ltd.; 2.5×41 cm) column. Linear gradient elution was carried out with 1 liter of aqueous acetone from 0 to 10%. The volume of each fraction was 10 ml. Fraction Nos. 48 to 53 were combined to give 60 ml of the active eluate (45,000 CCU/ml). Freeze drying provided 249 mg of yellow powder (8,000 CCU/mg).

For further purification, 150 mg of the said yellow powder was dissolved in a small amount of 0.01 M sodium phosphate buffer (pH 8.0) and passed through a 130 ml column (1.5×73 cm) of Sephadex G-10 (a bead-formed dextran gel prepared by crosslinking dextran fractions with epichlorohydrin; Pharmacia Fine Chemicals AB). Antibiotic PS-5 was developed with 0.01 M, pH 8.0, sodium phosphate buffer, the eluate being fractioned in a 2-ml amount. Thirty-six milliliters of the active eluate were obtained from fraction Nos. 38 to 55 (65,800 CCU/ml).

The Sephadex G-10 eluate was then subjected to QAE-Sephadex A-25 column chromatography (100 ml; 2.0×32 cm) followed by linear gradient elution with 1 liter of sodium chloride solution from 0 to 1.5%. The fraction volume was 10 ml. Five active fractions from Nos. 48 to 52 (50 ml; 22,000 CCU/ml) were combined as the active eluate.

This active eluate was carefully adjusted to pH 8.3 with 1% NaOH and charged on a 50-ml DIAION HP-20 column (1.2×44 cm).

The antibiotic PS-5 sodium salt was recovered in 5-ml fractions by linear gradient elution with 400 ml of aqueous acetone from 0 to 10%. Active fractions Nos. 39 to 41 were combined and lyophilized to yield 51 mg of white powder (21,000 CCU/mg).

This particular preparation of antibiotic PS-5 sodium salt showed the following physico-chemical properties:

(1) Color

White (2) Solubility

Soluble in water and substantially insoluble in acetone (3) Decomposition point

When measured in a Kofler micromelting point apparatus BY-1 (YAZAWA Scientific Mfg. Co., Ltd.) with the temperature raised at a rate of 1° C./minute, this preparation did not show a clear melting point. It began to turn yellow around 148° C. and gradually softened above 160° C. Around 203° C., the tint of the preparation slowly changed from yellow to brown. At 220° C., it was a brown resin.

(4) Ultraviolet absorption spectrum

Sixty microgram of antibiotic PS-5 sodium salt was dissolved in 3.0 ml of water and measured in a Hitachi Recording Sprectrophotometer Model EPS-3T (Hitachi Ltd.). The recorded chart is shown in FIG. 1. The following characteristic values were calculated:

$\lambda_{min.}{}^{H2O}$=ca. 246 nm($E_1$ $_{cm}{}^{1\%}$=82.0)

$\lambda_{max}{}^{H2O}$=ca. 301 nm($E_1$ $_{cm}{}^{1\%}$=267.5)

To an aqueous solution of this preparation (21,000 CCU/mg) in distilled water, a hydroxylamine solution (pH 7.5) was added to make a reaction mixture containing 21.3 μg/ml of antibiotic PS-5 sodium salt and 10 mM of hydroxylamine. After 30 minutes at 22° C., the reaction mixture lost ca. 94% of the initial optical density at 301 nm.

(5) Infrared absorption spectrum

Figure 2:
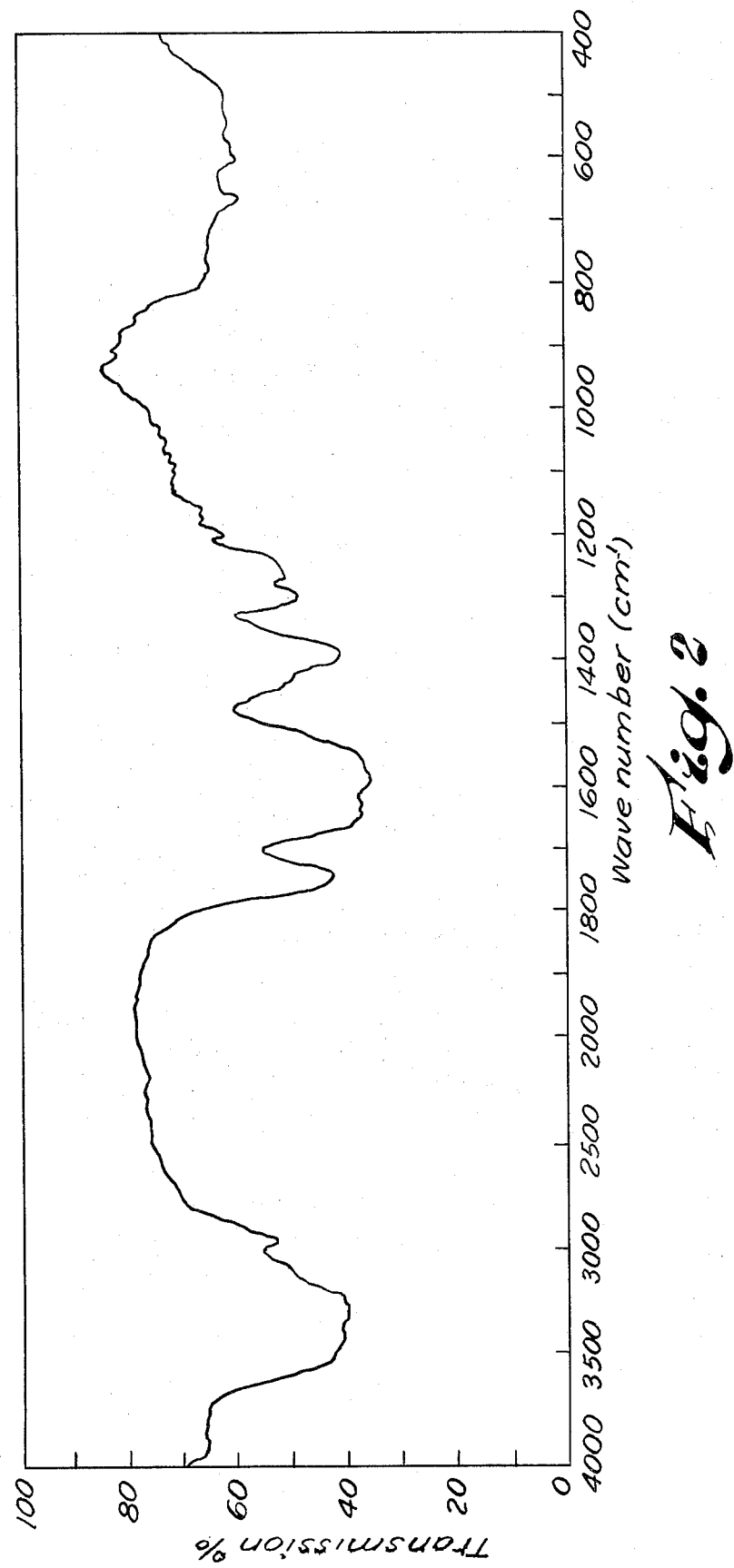
FIG. 2 is the infrared absorption spectrum of the antibiotic PS-5 sodium salt.

FIG. 2 shows the infrared absorption spectrum of antibiotic PS-5 sodium salt in KBr recorded on a Hitachi Infrared Spectrophotometer Model 215 (Hitachi, Ltd.). The following characteristic absorption maxima were located at the indicated wave numbers:

(i) ca. 1750 cm$^{-1}$ (—CO—in the beta-lactam ring)
(ii) ca. 1650 cm$^{-1}$ (—CO—in the amide bond)
(iii) ca. 1640-1540 cm$^{-1}$ (—COO$^\ominus$)

(6) Proton magnetic resonance spectrum

Figure 3:
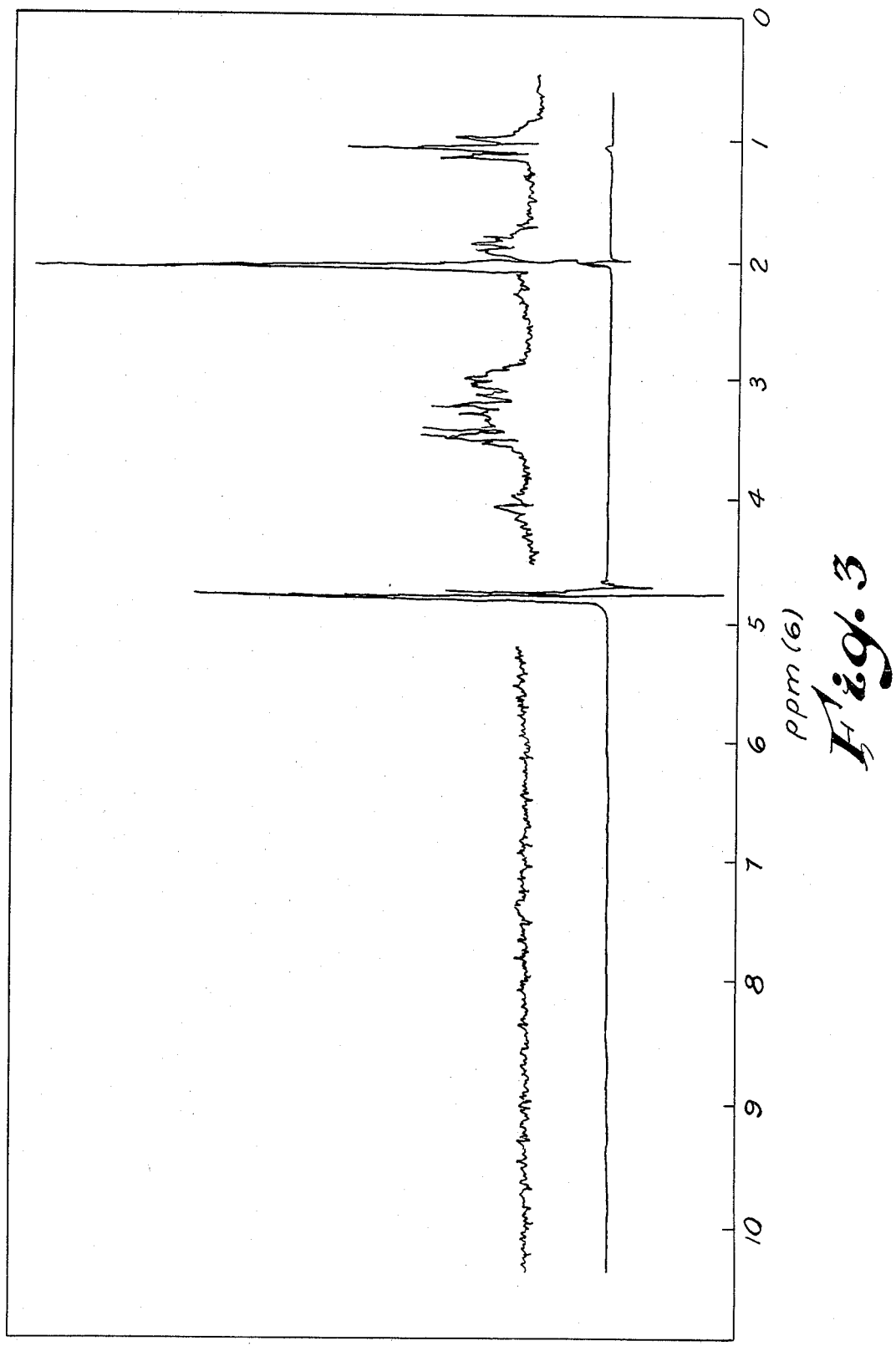
FIG. 3 is the proton magnetic resonance spectrum of the antibiotic PS-5 sodium salt.

The attached chart (FIG. 3) is the 100 Mhz proton magnetic resonance spectrum of antibiotic PS-5 sodium salt in deuterowater recorded in a JEOL NMR spectrometer JNM PS-100 (Japan Electron Optics Laboratory Co., Ltd.). The following characteristic signals were confirmed:

(i) triplet that has the center around 1.06 ppm (J=ca. 7.5 Hz)(CH$_3$—CH$_2$—)
(ii) multiplet in the region of 1.72-2.00 ppm (CH$_3$—CH$_2$—)
(iii) sharp singlet around 2.05 ppm (CH$_3$—CO—)
(iv) multiplets in the region of 2.88-3.58 ppm (—CH$_2$—,

(v) multiplet in the region of 3.9-4.20 ppm

(7) Color reaction

| Ehrlich reagent | positive |
| Iodine-chloroplatinic acid | positive |
| Ninhydrin | negative |

(8) Specific rotation

[α]$_D{}^{22}$+73.3 (c 1.59, 0.01 M, pH 8, sodium phosphate buffer)

(9) Thin layer chromatography (TLC)

The sodium salt of antibiotic PS-5 was subjected to TLC under the indicated conditions. Rf values were determined by bio-autography.

(a) AVICEL/SF cellulose TLC plate (American Viscose Corp.)

| Solvent system | Rf |
| --- | --- |
| n-butanol/ethanol/water = 7/7/6(v/v/v) | 0.94 |
| iso-propanol/water = 7/3(v/v) | 0.96 |

(b) Silicagel TLC plate (E. Merck, Darmstadt; Precoated silicagel plate 60 F$_{254}$)

| Solvent system | Rf |
| --- | --- |
| ethanol/water = 7/3(v/v) | 0.82 |

| Solvent system | Rf |
|---|---|
| n-propanol/water = 7/3(v/v) | 0.77 |

(10) Paper chromatography

The sodium salt of antibiotic PS-5 gave the following Rf values on Toyo Filter Paper No. 50 (Toyo Roshi kaisha Ltd.) under the indicated conditions:

| Solvent system | Rf |
|---|---|
| n-propanol/water = 7/3(v/v) | 0.68 |
| n-propanol/isopropanol/water = 7/7/6(v/v/v) | 0.70 |
| acetonitrile/water = 8/2(v/v) | 0.36 |
| acetonitrile/tris buffer/EDTA = (see foot note) | 0.34 |
| ethanol/water = 7/3(v/v) | 0.63 |

(a solvent mixture composed of 120 ml of acetonitrile; 30 ml of M/10 tris(hydroxymethyl)aminomethane-hydrochloric acid buffer (pH 7.5) and 1 ml of M/10 ethylenediamine tetraacetate (pH 7.5))

(11) High voltage paper electrophoresis

The sodium salt of antibiotic PS-5 was analyzed by high voltage paper electrophoresis under the indicated conditions. The apparatus was a product of Savant Instruments Inc. (High Voltage Power Supply, Model No. HV 3000V and Flat Plate Electrophoresis, Model No. EP 18A). The filter paper employed for this analysis was Toyo Filter Paper No. 50. The obtained results are as follows:

When electrophoresis was carried out for 30 minutes under cooling (below 4° C.) at a potential of 42 V/cm in a buffer (pH 8.6) containing 3.3 g of barbital and 25.5 g of barbital sodium in 3000 ml of water, the antibiotic PS-5 moved 28 mm to the anode.

(12) $^{13}C$-Magnetic resonance spectrum

Utilizing dioxane as the internal standard, the 20 MHz $^{13}C$-magnetic resonance spectrum of antibiotic PS-5 sodium salt in deuterium water was measured in a Varian CFT-20 spectrometer. The following characteristic signals were observed:
(1) 184.04 ppm
(2) 174.96
(3) 169.29
(4) 141.11
(5) 130.40
(6) 67.39 (dioxane)
(7) 60.19
(8) 55.63
(9) 40.41
(10) 40.00
(11) 31.49
(12) 22.62
(13) 22.46
(14) 11.36

The physico-chemical properties described above show that the molecular structure of the antibiotic PS-5 can be represented as follows:

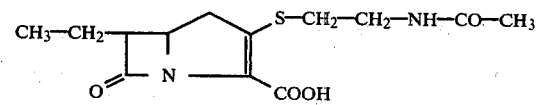

The following biological properties were confirmed with the antibiotic PS-5 sodium salt preparation of this example:

(1) Antimicrobial spectrum

The MIC values of antibiotic PS-5 sodium salt were determined on various pathogenic microorganisms including resistant strains by the broth dilution method utilizing the BRAIN HEART INFUSION BROTH 'Eiken' (EIKEN CHEMICAL CO., LTD.).

The antibiotic PS-5 sodium salt was dissolved in BRAIN HEART INFUSION BROTH 'Eiken' (EIKEN CHEMICAL CO., LTD.) (pH 7.0) at concentration in the range of 5–50 µg/ml, from which appropriate dilution series were made in the same liquid medium. The microorganisms listed in Table 8 were cultivated for 18 hours in BRAIN HEART INFUSION BROTH 'Eiken' at 28° C. and inoculated into the said dilution series of antibiotic PS-5 at a final inoculum size of $1 \times 10^5$ cells/ml. The cultures were allowed to stand at 35° C. for 20 hours, and then the growth of the microorganisms was read at each dilution of antibiotic PS-5. The minimum inhibitory concentration (MIC) represents the smallest concentration of the antibiotic PS-5 (sodium salt) where no propagation of the relevant microorganism was visually confirmed. As the controls, two known beta-lactam antibiotics, cephaloridine and cefoxitin were dissolved in brain heart infusion broth at pH 7.0 at concentrations ranging from 1 µg/ml to 100 µg/ml and then diluted to make several dilution series in the above mentioned liquid medium. These samples were treated as described above for the MIC determinations. Table 8 summarizes the obtained results. In addition to the MIC values of antibiotic PS-5, those of cephaloridine and cefoxitin are included for reference.

TABLE 8

| | Minimum inhibitory concentration µg/ml | | |
|---|---|---|---|
| Microorganism | Antibiotic PS-5 | Cepha-loridine | Cefoxitin |
| Staphylococcus aureus | | | |
| EDA 209 P | 0.16 | 0.031 | 1.25 |
| Smith | 0.31 | 0.031 | 2.50 |
| Russell | 0.31 | 0.125 | 2.50 |
| Bx-1633 | 0.16 | 0.031 | 1.25 |
| Diplococcus pneumoniae Type III[4]* | 0.02 | 0.031 | 1.25 |
| Streptococcus pyogenes NY-5[4]* | 0.08 | 0.008 | 0.63 |
| Bacillus subtilis ATCC 6633 | 0.16 | 0.031 | 1.25 |
| Escherichia coli K 12 | 2.5 | 2.5 | 2.5 |
| Alcaligenes faecalis B-326 | 0.78 | 6.25 | 1.56 |
| Citrobacter freundii E-9* | 3.13 | >100 | >100 |
| Serratia marcescens S-18* | 6.25 | >100 | 50 |
| Klebsiella pneumoniae K-2* | 3.13 | 6.25 | 6.25 |
| Enterobacter sp. E-8* | 3.13 | 3.13 | 12.5 |
| Enterobacter cloacae E-16* | 12.5 | >100 | >100 |
| Enterobacter aerogenes E-19* | 6.25 | >100 | >100 |
| Proteus vulgaris P-5* | 12.5 | >100 | 12.5 |
| Proteus mirabilis P-6[2]* | 6.25 | 12.5 | 12.5 |
| Proteus rettgeri P-7[3]* | 3.13 | 100 | 6.25 |
| Proteus sp. P-22 | 6.25 | >100 | 12.5 |

TABLE 8-continued

| Microorganism | Minimum inhibitory concentration μg/ml | | |
|---|---|---|---|
| | Antibiotic PS-5 | Cepha-loridine | Cefoxitin |
| Providencia sp. P-8[2*] | 6.25 | >100 | 25.0 |

Note:
*beta-lactamase producer;
[2*]resistant to kanamycin, gentamicin and tobramycin;
[3*]resistant to gentamicin and tobramycin
[4*]10% horse blood supplemented into the medium (2) Potentiation of the antimicrobial activity of known beta-lactam compounds against beta-lactam-resistant microorganisms (A) Ten milliliters of molten nutrient agar containing 50 μg/ml of penicillin G or cephaloridine, 0.8% of Kyokuto Nutrient Broth Powder and 1.0% of Difco Bacto-Agar (pH 7.0) were seeded with the beta-lactam-resistant, beta-lactamase-producing microorganisms indicated in Tables 9 and 10, and poured in a 9-cm Petri dish to provide the bio-assay agar plate. On this assay plate, 8-mm pulp discs containing 25 μl each of antibiotic PS-5 solutions at the indicated concentrations were placed and incubated at 35° C. for 18 hours before reading the inhibition zones. The control assay plate was similarly prepared without penicillin G nor cephaloridine. As reference antibiotics, penicillin G, ampicillin, oxacillin and cefazolin were disc-assayed under the same conditions. Tables 9 and 10 summarize the observed results.

TABLE 9

| Beta-lactam-resitant microorganism | Antibiotic PS-5 (μg/ml) | Inhibition zone(mm) | |
|---|---|---|---|
| | | Without pen. G | With pen. G |
| Proteus vulgaris P-5 | 318 | 16.0 | 26.6 |
| | 159 | 14.0 | 24.5 |
| | 100 | 10.3 | 22.2 |
| | 79.5 | 0 | 18.3 |
| Enterobacter sp. E-8 | 318 | 20.1 | 20.0 |
| | 159 | 17.2 | 17.5 |
| | 100 | 13.8 | 13.8 |
| | 79.5 | 11.0 | 11.0 |
| Citrobacter freundii E-9 | 318 | 20.8 | 23.0 |
| | 159 | 17.2 | 19.2 |
| | 100 | 13.2 | 15.2 |
| | 79.5 | 10.4 | 13.1 |
| Serratia marcescens S-18 | 318 | 21.3 | 22.1 |
| | 159 | 17.8 | 22.0 |
| | 100 | 13.0 | 16.1 |
| | 79.5 | 0 | 13.8 |
| Proteus sp. P-22 | 318 | 13.6 | 21.4 |
| | 159 | 11.7 | 18.2 |
| | 100 | 0 | 13.8 |
| | 79.5 | 0 | 12.8 |

TABLE 10

| Beta-lactam-resitant microorganism | | Inhibition zone (mm) | |
|---|---|---|---|
| | | Without CER* | With CER* |
| | Antibiotic PS-5 (μg/ml) | | |
| Enterobacter sp. E-18 | 318 | 21.0 | 21.9 |
| | 159 | 18.2 | 19.4 |
| | 100 | 16.1 | 18.0 |
| | 79.5 | 15.1 | 17.6 |
| Citrobacter freundii E-9 | 318 | 22.5 | 24.6 |
| | 159 | 17.4 | 22.3 |
| | 100 | 17.4 | 21.6 |
| | 79.5 | 16.0 | 19.4 |
| Serratia marcescens | 318 | 21.0 | 26.1 |
| | 159 | 17.0 | 24.8 |
| | 100 | 16.8 | 23.3 |
| | 79.5 | 14.8 | 22.3 |
| Proteus vulgaris P-5 | 318 | 18.5 | 25.2 |
| | 159 | 15.2 | 24.0 |
| | 100 | 13.7 | 22.0 |
| | 79.5 | 12.5 | 21.8 |
| | Penicillin G (μg/ml) | | |
| Proteus vulgaris P-5 | 10,000 | 14.9 | 14.5 |
| | 2,500 | 0 | 0 |
| | 625 | 0 | 0 |
| | Ampicillin (μg/ml) | | |
| Proteus vulgaris P-5 | 10,000 | 14.7 | 12.9 |
| | 2,500 | 0 | 0 |
| | 625 | 0 | 0 |
| | Oxacillin (μg/ml) | | |
| Proteus vulgaris P-5 | 10,000 | 0 | 0 |
| | 2,500 | 0 | 0 |
| | 625 | 0 | 0 |
| | Cefazolin (μg/ml) | | |
| Proteus vulgaris P-5 | 10,000 | 14.6 | 12.0 |
| | 2,500 | 0 | 0 |
| | 625 | 0 | 0 |

*CER = Cephaloridine

As apparent from the above results, when penicillin G or cephaloridine at a concentration below the detactable limit was combined with antibiotic PS-5 at a concentration below the threshold of disc assay, an inhibition zone was observed, which means the potentiation of the activity of penicillin G and cephaloridine with antibiotic PS-5. In contrast, penicillin G, ampicillin, oxacillin and cefazolin could not increase the antimicrobial activity of cephaloridine.

(B) The subsequent experiment was carried out to prove that the potentiating effect of antibiotic PS-5 was synergistic.

On an assay plate of nutrient agar seeded by a beta-lactam-resistant strain of Proteus vulgaris P-5 (beta-lactamase producer), two filter paper strips containing penicillin G or cephaloridine and two strips containing antibiotic PS-5 were applied to form a square where two strips of the same antibiotic were contacted at one corner. The antimicrobial activity was read after incubation for 18 hours at 35° C. When suitable concentrations of penicillin G or cephaloridine and antibiotic PS-5 were chosen, the inhibition area was observed only at the corners where both antibiotic PS-5 and penicillin G or cephaloridine were present, but not at the corners where antibiotic PS-5, penicillin G or cephaloridine was solely present. This fact can be explained by synergism between the antibiotic PS-5 and penicillin G or cephaloridine. That is, when two kinds of compounds were combined at concentrations that were low enough not to give an inhibition zone with a component alone, the large inhibition thus appearing with the combination was due to synergism.

(3) In vivo activity

The therapeutic activity of the antibiotic PS-5 sodium salt was studied by treating mice intraperitoneally infected with $5 \times 10^5$ cells/mouse of Staphylococcus aureus Smith. Soon after the infection, an aqueous solution of the antibiotic PS-5 sodium salt was subcutaneously injected. In male ddy mice (Shizuoka), the 50% curative dose of this preparation was found to be 2.45 mg/kg.

(4) Toxicity

An aqueous solution of the antibiotic PS-5 sodium salt was intraperitoneally administered to male ddy mice (Shizuoka) at the dose of 500 mg/kg. No dead was recorded.

(5) Beta-lactamase-inhibition activity

The beta-lactamase-inhibition activity of antibiotic PS-5 was examined on the hydrolysis of penicillin G by beta-lactamase from *Proteus vulgaris* P-5 in the following manners:

(A) Reagent (1) Substrate: penicillin G potassium salt 1 μmole/ml(=372.3 μg/ml) in 25 mM phosphate buffer (pH 6.8)
(2) Beta-lactamase: inducible beta-lactamase of *Proteus vulgaris* P-5 which was purified by CM-cellulose Column chromatography
(3) Inhibitor: the antibiotic PS-5 sodium salt preparation 0.6 μmole/ml (=192 μg/ml)
(4) 25 mM, pH 6.8 phosphate buffer

(B) Reaction composition and assay conditions

The substrate (=penicillin G), the inhibitor (=antibiotic PS-5) and the buffer were mixed well at 30° C. in the amounts indicated in the subsequent table (Table 11).

The reaction was initiated at once by adding the indicated amounts of beta-lactamase at 30° C.

TABLE 11

|  | (I) Enzyme Standard (H) | (II) Enzyme Standard (L) | (III) Inhibition by antibiotic(PS-5)(H) | (IV) Inhibition by antibiotic PS-5(L) |
|---|---|---|---|---|
| (1) Penicillin G (1μ mole/ml) | 2.5 moles (2.5 ml) | 2.5 moles (2.5 ml) | 2.5 moles (2.5 ml) | 2.5 moles (2.5 ml) |
| (2) Antibiotic PS-5 (0.6 μ mole/ml) | 0 | 0 | 0.105 mole* (0.175 ml) | 0.06 mole** (0.100 ml) |
| (3) Phosphate buffer (25 mM, pH 6.8) | (0.5 ml) | (0.5 ml) | (0.325 ml) | (0.40 ml) |
| (4) Beta-lactamase | (0.040 ml) | (0.020 ml) | (0.040 ml) | (0.040 ml) |

Molar ratio of the substrate to the inhibitor:
*24 : 1
**42 : 1

The hydrolysis of penicillin G was traced by measuring the decrease in optical density at 240 nm, assuming that the differential molar extinction of penicillin G at 240 nm was 556 which was derived from several preliminary experiments.

(C) Results

Figure 4:
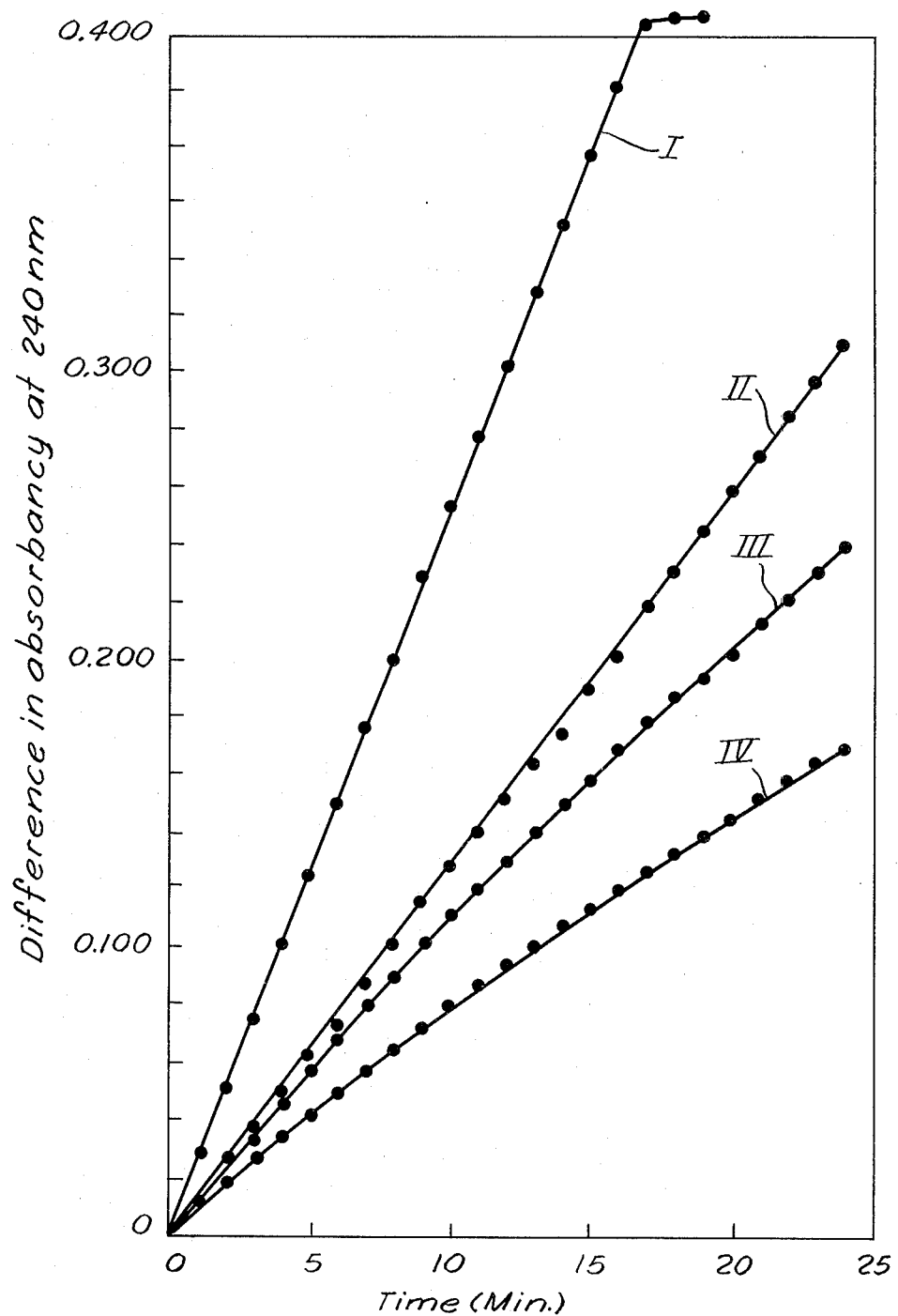
FIG. 4 is time courses of degradation of penicillin G by beta-lactamase of *Proteus vulgaris* P-5 which shows the inhibitory activity of the antibiotic PS-5 prepared in Example 9 of this invention.

FIG. 4 shows the time course of hydrolysis of penicillin G in the absence of the inhibitor (antibiotic PS-5) under the above specified conditions. A strong inhibition of *Proteus vulgaris* penicillinase by antibiotic PS-5 is very clear in FIG. 4; that is, when 1/42 equivalent of antibiotic PS-5 was present in penicillin G as the substrate, more than 50% of the activity of *Proteus vulgaris* P-5 beta-lactamase was inhibited.

EXAMPLE 10

METHOD FOR PREPARATION OF THE TRITYL ESTER OF ANTIBIOTIC PS-5

One hundred-sixty liters of the broth filtrate prepared as described in Example 3 was treated as described in Example 4 to produce 30.0 g of yellowish brown lyophylized powder of the antibiotic PS-5 sodium salt (specific activity 27 CCU/mg). This powder was dissolved in 100 ml of dimethylformamide and 3.0 g of triethylamine were added. Under cooling with ice, 9.0 g of trityl chloride were added to the reaction mixture while the temperature of the solution was maintained below 5° C. After stirring for 12 hours at 5° C., all the activity of the antibiotic PS-5 was converted to the tritylation product. The reaction solution was poured in 1000 ml of 0.5 M phosphate buffer (pH 6.8) and then extracted three times with 1000 ml each of ethyl acetate. The ethyl acetate extracts were combined, dehydrated over anhydrous sodium sulfate and evaporated to dryness under reduced pressure. The evaporation residue was dissolved in 20 ml of benzene and passed through a Bio-Beads S-X3 (a porous styrene-divinylbenzene copolymer beads for gel permeation, molecular weight exclusion limit: 2000, produced by BIO-RAD Laboratories) column (4.5×60.0 cm) that had been preequilibrated with benzene. The column was developed with benzene. The active fraction that showed an antibiotic activity of the Comamonas assay plate was concentrated to dryness under reduced pressure. The obtained residue was dissolved in 1 ml of benzene and charged on a silicagel column (silicagel 60; 70-230 mesh ASTM; E. Merck, Darmstadt) (25 g; 1.5×24.0 cm). After washing with a benzene-ethyl acetate mixture (10:1) to remove the residual reagents, the activity was eluted with a benzene-ethyl acetate (1:2) mixture. The active eluate was evaporated to dryness under reduced pressure and again dissolved in 0.5 ml of benzene. The benzene solution was applied on a neutral aluminum oxide column (Aluminum Oxide Woelm neutral; M. Woelm; 20 g, 0.9×22.0 cm) and developed with a benzene-ethyl acetate mixture at varied mixing ratios (10:1, 6:1, 4:1, 3:1, 2:1 and 1:1). Active eluates were combined and evaporated to dryness under reduced atmosphere. The evaporation residue was dissolved in 0.3 ml of benzene and charged on a silicagel column (10 g; 0.9×22.0 cm; described above). After impurities were removed with a benzene-ethyl acetate mixture (10:1), the activity was eluted with a benzene-ethyl acetate mixture (1:2) and concentrated to solid powder under reduced pressure. The obtained powder was dissolved in 0.5 ml of benzene and purified on a Bio-Beads S-X3 column (1.2×96 cm) with benzene as developing solvent. The active effluent was evaporated to dryness in vacuo.

The obtained dry powder was dissolved in 0.5 ml of acetone and subjected to gel filtration with a Sephadex LH-20 column (a bead-formed dextran gel prepared by crosslinking dextran chains by hydroxypropylation;

produced by Pharmacia Fine Chemical AB) (1.2×96.0 cm) that had been pre-swolled in acetone. The active fraction was evaporated to dryness to give 23 mg of white powder. The recrystallization of this powder in a benzene-hexane mixture provided 12 mg of colorless crystalline powder of the product (10,800 CCU/mg). The colorless crystalline powder of the aimed product, that is, the trityl ester of antibiotic PS-5 of the present invention, had the following physico-chemical properties:

(1) Color

Colorless (2) Solubility

The solubility of the tritylation product of the antibiotic PS-5 was determined by dissolving under skaking 5 mg each of the tritylation product of the antibiotic PS-5 in 0.1 ml each of the test solvents at 20° C. The results were as shown below:

Substantially insoluble in water, n-hexane and petroleum ether (boiling point in the range of 30°–60° C.).

Highly soluble in benzene, ethyl acetate, chloroform, methanol, ethanol, acetone, dimethylformamide (DMF) and dimethylsulfoxide (DMSO).

(3) Stability

The trityl ester of antibiotic PS-5 was dissolved in one volume of methanol and then diluted with 9 volumes of distilled water as soon as possible to provide a solution of 125 CCU/ml. A tenth molar dipotassium phosphate solution was adjusted with 5 N phosphoric acid or 5 N sodium hydroxide to the indicated pH's in the range of 3–9.

To one milliliter each of the phosphate buffers, one milliliter each of the said solution of the trityl ester of antibiotic PS-5 was added and, if necessary, the pH value of the mixture was readjusted with phosphoric acid or sodium hydroxyde to the desired pH value. The mixture solution was kept in a water bath at 60° C. for 30 minutes, cooled with running water and neutralized to pH 7.0 with a small amount of phosphoric acid or sodium hydroxide.

The control solution (pH 7.0) was kept in an ice bath for the experimental period. The residual antibiotic activity was assayed by the routine disc assay method with *Comamonas terrigena* B-996 as the test microorganism. The percent activity of the heat-treated solutions to the control solution is shown in Table 12.

TABLE 12

| pH | 3.0 | 4.0 | 5.0 | 6.0 | 7.0 | 8.0 | 9.0 |
|---|---|---|---|---|---|---|---|
| Residual activity (%) | 0 | 0 | 6.5 | 79.0 | 100 | 100 | 100 |

From these results it is clear that the trityl ester of antibiotic PS-5 is stable in an aqueous solution at 60° C. for 30 minutes at a pH in the range of 6.0–9.0.

In addition, no substantial loss of activity was confirmed after an aqueous solution of the tritylation product of antibiotic PS-5 was incubated at pH 7.5 for 90 minutes at 60° C.

(4) Melting point

It was measured in a Kofler micro melting point apparatus BY-1 (Yazawa Scientific Mfg. Co., Ltd.), the temperature being elevated at a rate of 1° C./minute. The tritylation product of antibiotic PS-5 melted at 83.5°–85.5° C. and gradually turned brown above 140° C.

(5) Ultraviolet absorption spectrum

Figure 5:
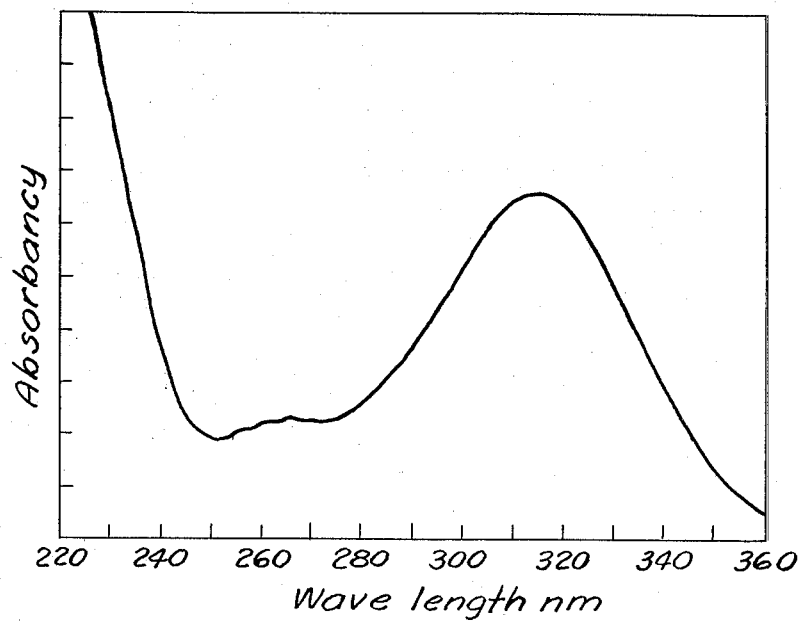
FIG. 5 is the ultraviolet absorption spectrum of the trityl ester of the antibiotic PS-5 prepared in Example 10 of this invention.

The ultravioler absorption spectrum of the tritylation product of antibiotic PS-5 of the present invention was recorded in a Hitachi Rocording Spectrophotometer Model EPS-3T (Hitachi, Ltd.) at a concentration of 128 μg/3 ml of methanol (FIG. 5).

$\lambda_{max}{}^{MeOH} = 315.5$ nm ($E_1{}_{cm}{}^{1\%} = 156$)

(6) Infrared absorption spectrum

Figure 6:
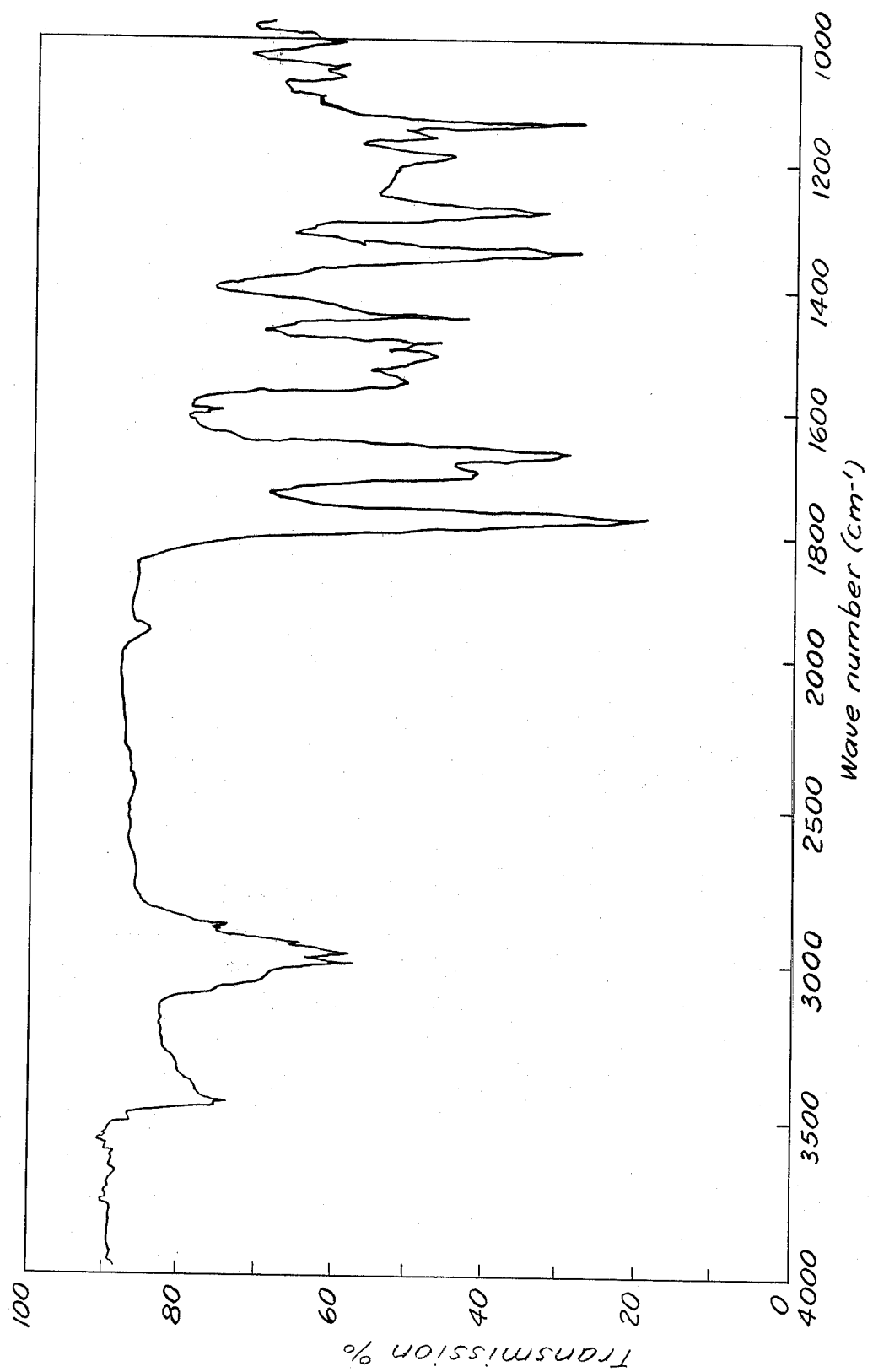
FIG. 6 is the infrared absorption spectrum of the said trityl ester of antibiotic of antibiotic PS-5.

The attached FIG. 6 shows the infrared absorption spectrum of the tritylation product of antibiotic PS-5 (4.5 mg) in 0.6 ml of chloroform recorded in a Hitachi Infrared Spectrophotometer Model 215 (Hitachi, Ltd.). The characteristic absorption maxima were observed at the following wave number:
3430
3100–3000 (C-H of the phenyl group)
2990
2950
1770 (C=O of the beta-lactam ring)
1695 (—CO— of the amide bond)
1665 (—CO—O— of the ester bond)
1445
1340
1275
1130 cm$^{-1}$ (7) Proton magnetic resonance spectrum The attached figure (FIG. 7) shows the 100 MHz proton magnetic resonance spectrum of antibiotic PS-5 trityl ester recorded with 4.5 mg of said trityl ester in 0.3 ml of deuterochloroform, utilizing a JEOL NMR spectrometer JNM PS-100 (Japan Electron Optics Laboratory Co., Ltd.). The most characteristic signals are the following:
triplet around 1.10 ppm (J=ca. 7.0 Hz)
singlet at 1.86 ppm
multiplet in the region of 7.10–7.56 ppM (protons in the benzene ring of the trityl group)

(8) Elementary analysis.

Three and a half milligram of the tritylation product of antibiotic PS-5 were dried at room temperature for 4 hours at a reduced pressure of $1 \times 10^{-2}$ mm Hg and subjected to the elementary analysis to give the the following analysis data:
found:
C 61.89%
H 5.78%
N 4.48%
S 4.62%

(9) Coloration reaction:

| Enrlich reagent | positive |
|---|---|
| Triphenyltetrazolium chloride | negative |
| Ferric chloride | negative |
| Ferric chloride-iodine | negative |
| Iodine-chloroplatinic acid | positive |
| Hydroxylamine-ferric chloride | positive |
| Chlorine-tolidine | positive |
| Ninhydrin | negative |

(10) Thin layer chromatography (TLC)

The trityl ester of the antibiotic PS-5 gave the following Rf values under the indicated conditions. The site of migration was revealed by bioautography on *Comamonas terrigena* B-996.

(a) Silica gel TLC

Plate: Pre-coated silicagel plate 60 $F_{254}$, E. Merck, Darmstadt Solvent system: benzene/acetone (2/1)
Rf: 0.29

(b) Cellulose TLC

Plate: EASTMAN CHROMAGRAM Sheet 13254 CELLULOSE with Fluorescent

| Indicator (No. 6065) solvent: | Rf: |
|---|---|
| Upper phase of n-butanol/ethanol/water (4/1/5) | 0.56 |
| n-butanol | 1.0 |
| Isopropanol/water (8/7) | 0.91 |
| Isopropanol/water (½) | 1.0 |

The molecular structure of the antibiotic PS-5 and the above specified physico-chemical properties support the following structure for the trityl ester of the antibiotic PS-5.

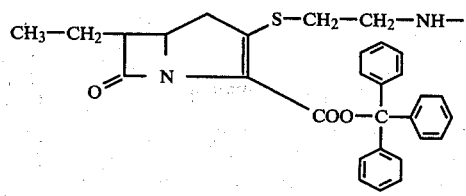

The biological properties of the trityl ester of antibiotic PS-5 are shown in the following:

(1) Antimicrobial spectrum

The MIC (minimum inhibitory concentration) values of the compound were determined on various pathogenic microorganisms including several resistant strains, utilizing the broth dilution method in BRAIN HEART INFUSION BROTH 'Eiken' (EIKEN CHEMICAL CO., LTD.).

More particularly, the trityl ester of antibiotic PS-5 was dissolved in a small amount of methanol and diluted as soon as possible in BRAIN HEART INFUSTION BROTH 'Eiken' (pH 7.0 (EIKEN CHEMICAL CO., LTD.) until the concentration of the trityl ester of antibiotic PS-5 was in the range of 40 µg/ml to 20 µg/ml. The concentration of methanol in the final solution did not exceed 10%. This solution was diluted in a two-fold geometric series. The microorganisms listed in Table 13 were cultivated for 18 hours at 28° C. in the BRAIN HEART INFUSION BROTH 'Eiken' and inoculated into the series of dilutions at a final inoculum size of $1 \times 10^5$ cells/ml. The results were read after incubation at 35° C. for 20 hours. The minimum inhibitory concentration (MIC) values means the lowest concentration unit of the trytylation product of the antibiotic PS-5 was no growth of the corresponding microorganism was observed under the above described conditions. As the control antibiotics, the solutions of ampicillin and cephaloridine were prepared in BRAIN HEART INFUSION BROTH 'Eiken' (pH 7.0) at a concentration of 100 µg/ml and treated same as the test compound of the present invention.

Table 13 summarizes the MIC values of the trityl ester of antibiotic PS-5 together with those of ampicillin and cephaloridine as the control antibiotics.

As apparent from the above described Table, the trityl ester of antibiotic PS-5 exhibits a broad antimicrobial spectrum and particularly has a strong antibiotic activity on a various beta-lactam-resistant (beta-lactamase-producing) strains of microorganisms.

TABLE 13

| | MIC (µg/ml) | | |
|---|---|---|---|
| Microorganism | Trityl PS-5 | Ampicillin | Cephaloridine |
| *Staphylococcus aureus* FDA 209p | 0.17 | 0.20 | 0.04 |
| *Staphylococcus aureus* Smith | 0.27 | 0.20 | 0.04 |
| *Diplococcus pneumoniae* Type III | 0.08 | 0.04 | 0.01 |
| *Streptococcus pyogenes* NY-5 | 0.17 | 0.02 | 0.01 |
| *Sarcina lutea* S-19 | 0.27 | 0.05 | 0.05 |
| *Escherichia coli* K12 | 5.37 | 3.13 | 2.5 |
| *Alcaligenes faecalis* B-326 | 1.25 | 6.25 | 6.25 |
| *Citrobacter freundii* E-9 | 5.0 | >100 | >100 |
| *Serratia marcescens* S-18 | 10.0 | 50 | >100 |
| *Klebsiella pneumoniae* K-2 | 10.7 | >100 | 10.0 |
| *Enterobacter sp.* E-8 | 10.0 | >100 | >100 |
| *Enterobacter cloacae* E-16 | 10.0 | >100 | >100 |
| *Enterobacter aerogenes* E-19 | 8.7 | >100 | >100 |
| *Proteus vulgaris* P-5 | 21.5 | >100 | >20.0 |
| *Proteus mirabilis* P-6 | 21.5 | 3.13 | 10.0 |
| *Proteus rettgeri* P-7 | 10.0 | 50.0 | 50.0 |
| *Pseudomonas aeruginosa* P-1 | >43.0 | 50.0 | >20.0 |

(2) Potentiation effect of the trityl ester of antibiotic PS-5 on the antibiotic activity of penicillin and cephalosporin compounds against resistant microorganisms (A) Assay Petri dishes (9 cm in diameter) containing resistant microorganisms were prepared by overlaying 10 ml of the molten nutrient agar seeded with beta-lactam-resistant (beta-lactamase-producing) microorganisms, on the solid base layer of nutrient agar (pH 7.0) (15 ml) containing 50 µg/ml of penicillin G or cephaloridine. As described before, the antibiotic solutions to be tested were applied in a 25 µl amount on an 8 mm pulp disc and placed on the said assay dishes. After incubation for 18 hours at 35° C., the inhibition halos were measured and compared with the results on the corresponding assay dished containing neither penicillin G nor cephaloridine. Table 14 summarizes the results. From the data in Table 14, it is very clear that the combination of the tritylation product of antibiotic PS-5 at a concentration below the lower limit of disc assay, with penicillin G or cephaloridine, at a concentration below said limit, produced a significant halo of inhibition. This fact clearly proves the potentiation of the antibiotic activity of penicillin G or cephaloridine with the tritylation product of antibiotic PS-5.

TABLE 14

| | Halo of inhibition (mm) | | |
|---|---|---|---|
| Beta-lactam-resistant microorganism | Trityl PS-5 µg/ml | Control | Penicillin G added |
| *Proteus vulgaris* P-5 | 42 | 0 | 27.0 |

| | | Control | Cephaloridine added |
|---|---|---|---|
| *Proteus vulgaris* P-5 | 50 | 0 | 15.0 |
| | 100 | 11.0 | 18.0 |
| *Proteus sp.* P-22 | 50 | 0 | 11.5 |
| | 100 | 0 | 13.5 |

TABLE 14-continued

| | | | |
|---|---|---|---|
| Citrobacter freundii E-9 | 50 | 13.0 | 15.5 |
| | 100 | 16.0 | 18.0 |

(B) As another proof of potentiation, the antimicrobial synergism of the tritylation product of antibiotic PS-5 with cephaloridine was confirmed by the broth dilution method on a β-lactam-resistant strain of *Proteus vulgaris*. First of all, five samples of stock solutions containing cephaloridine and the trityl ester of antibiotic PS-5 at the varied concentrations indicated in Table 15 were prepared, utilizing BRAIN HEART INFUSION BROTH 'Eiken' (pH 7.0) as the solvent.

TABLE 15

| Stock solution No. | Trityl ester of antibiotic PS-5 | Cephaloridine |
|---|---|---|
| 1 | 100 μg/ml | 0 μg/ml |
| 2 | 75 | 500 |
| 3 | 50 | 1000 |
| 4 | 25 | 1500 |
| 5 | 0 | 2000 |

From each stock solution, three samples of sub-stock solutions were prepared by diluting at rates of 1:2, 2:5 and 3:10, in the said brain heart infusion broth. In total, 15 samples of sub-stock solutions were obtained. With each sub-stock solution, 15 steps of the 2-fold dilution were carried out in the brain heart infusion broth. To each of the 15 dilutions, *Proteus vulgaris* P-5 was inoculated at a final concentration of $1 \times 10^5$ cells/ml and incubated at 35° C. for 20 hours. The minimum inhibitory dilution was read in each stock solution. The obtained results are summarize in Table 16.

TABLE 16

| Stock solution No. | Trityl PS-5: cephaloridine | MIC Trityl PS-5:CER | Total amount of the antibiotics |
|---|---|---|---|
| 1 | 100:0(μg) | 10 + 0 (μg) | 10.0 (μg) |
| 2 | 75:500 | 3.75 + 25 | 28.75 |
| 3 | 50:100 | 1.88 + 37.5 | 39.38 |
| 4 | 25:1500 | 1.25 + 75 | 76.25 |
| 5 | 0:200 | 0 + 1000 | 1000 |

Though the synergism in understandable from Table 16, it will be more easy to realize the synergistic effect of the trityl ester of the antibiotic PS-5 on cephalordine when the MIC results are expressed in term of the relative value to MIC of each antibiotic alone. Table 17 evidently shows the synergism between the two antibiotic compounds, wherein the MIC values of each antibiotic alone is expressed as 100.

TABLE 17

| Stock Solution No. | Trityl PS-5: cephaloridine | Relative MIC value (Trityl PS-5 + CER = Total) |
|---|---|---|
| 1 | 100:0 (μg) | 100 + 0 = 100 |
| 2 | 75:500 | 37.5 + 2.5 = 40 |
| 3 | 50:1000 | 18.8 + 3.75 = 22.55 |
| 4 | 25:1500 | 12.5 + 7.5 = 20 |
| 5 | 0:2000 | 0 + 100 = 100 |

The above Table 17 shows that the synergistic effect of the trityl ester of the antibiotic PS-5 on cephaloridine is very clear. That is, when *Proteus vulgaris* P-5 that is resistant to beta-lactam compounds because of beta-lactamase production was employed as the test microorganism, the combination of 7.5% of the MIC of cephaloridine with 12.5% of the MIC of the trityl ester of antibiotic PS-5 inhibit the growth of the said test microorganism.

(3) In vivo activity:

The in vivo activity of the tritylation product of the antibiotic PS-5 was measured in mice intraperitoneally infected with $5 \times 10^3$ cells/mouse of *Staphylococcus aureus* Smith. The trityl ester of the antibiotic PS-5 was subcutaneously injected just after infection.

The 50% curative dose in male ddy mice (SHOZUOKA) was 2.55 mg/kg (27,540 CCU/kg).

(4) Beta-lactamase-inhibition activity (A) Assay method

The $I_{50}^{CER}$ value of hydrolysis of cephaloridine by beta-lactamase for 10 minutes (from one minute to ten minutes after the incubation is started). The rate of hydrolysis of cephaloridine is measured by the decrease of optical density at 225 mμ. For routine inhibition assays, beta-lactamase of *Citrobacter freundii* E-9 and *Proteus vulgaris* P-5 were employed after purification by affinity chromatography with cephalexin-Sepharose 4B.

(B) Reagent

Buffer: 0.1 M phosphate buffer (Na-K phosphate) (pH 6.8)

Substrate: 0.05 micromole/ml in phosphate buffer

Beta-lactamase: The enzyme was diluted enough to give a fall of ca. 0.1 optical density unit per 10 minutes at 255 mμ in the absence of an inhibitor. (Apparatus: Hitachi Spectrophotometer UV-VIS 139, Hitachi, Ltd.).

(This can hold one control cuvette and three sample cuvettes. Four 1 cm quarz cuvettes (3 ml in volume) were employed. The temperature was maintained at 30° C. during the reaction).

Inhibitor: Dilution was carried out in 0.1 M phosphate buffer (pH 6.8) or in dimethylsulfoxide (DMSO). The control cuvette contained the same amount of diluting solution without inhibitor as the sample cuvette.

Reaction conditions: The enzyme-inhibitor mixture of the following composition was preincubated for 15 minutes at 30° C.

| | |
|---|---|
| phosphate buffer | 100 μl |
| enzyme | 0.5–2.0 μl |
| inhibitor | 0.5–40 μl |

After pre-incubation, the substrate solution (pre-warmed at 30° C.; 3.0 ml) was added and quickly mixed to start the reaction. The reaction was followed by recording the change of optical density at 255 mμ for 10 minutes at 30° C. The value of $I_{50}^{CER}$ (μg/ml) was determined by diluting the inhibitor untill the dilution gave 50% of the rate of hydrolysis of cephaloridine recorded in the no-inhibitor control for 10 minutes (from 1 minute to 11 minutes after the substrate was added).

(C) Results

Under the above described reaction conditions, the following $I_{50}^{CER}$ values were obtained with the trityl ester of the antibiotic PS-5:

| Beta-lactamase from: | $I_{50}^{CER}$ (μg/ml) |
|---|---|
| *Proteus vulgaris* P-5 | 0.060 |
| *Citrobacter freundii* E-9 | 0.80 |

Thus, 50% of the hydrolysis of cephaloridine was inhibited with 0.060 μg/ml and 0.80 μg/ml of the tritylation product of the antibiotic PS-5 on assay by beta-lactamases of *Proteus vulgaris* P-5 and *Citrobacter freundii* E-9, respectively, under the above specified conditions.

(5) Toxicity

The trityl ester of the antibiotic PS-5 did not provoke any dead in male ddy mice (Shizuoka) when administered at the intraperitoneal dose of 500 mg/kg.

EXAMPLE 11

METHOD FOR PREPARATION OF THE TRITYLATION PRODUCT OF ANTIBIOTIC PS-5

The brownish yellow antibiotic PS-5 sodium salt powder (715 mg; 235 CCU/mg) prepared by the same method as described in Example 7 was dissolved in 3.5 ml of hexamethylphosphatriamide (HMPA). After addition of 70 mg of triethylamine under cooling with ice, 250 mg of trityl bromide were added to the mixture at a temperature below 10° C. The mixture was stirred at 10° C. for 7 hours to complete the tritylation reaction. The reaction mixture was poured into 50 ml of ice water and allowed to stand until solid ice melted.

The trityl ester of antibiotic PS-5 was extracted three times with 15 ml each of benzene and treated as described in Example 10 to give 9.4 mg of colorless crystalline powder of the desired product. The physico-chemical properties of this preparation were practically identical with those in Example 10.

EXAMPLE 12

PREPARATION OF THE TRITYLATION PRODUCT OF ANTIBIOTIC PS-5 IN THE PRESENCE OF A CROWN ETHER

The crude brownish white lyophilization powder (10.1 g) prepared by the same process as described in Example 5 was suspended in 200 ml of methylene chloride and dissolved with stirring under addition of 1 ml of 15-Crown-5(Nippon Soda Co., Ltd.). While the temperature of the solution was kept below 5° C. with ice, 8.5 g of trityl chloride were added. The reaction mixture was warmed to room temperature and stirred for three hours at that temperature. After filtration, the filtrate was evaporated to dryness under reduced pressure. The residue was dissolved in 10 ml of benzene at once, filtered and purified by the identical procedure to that described in Example 10 to yield a colorless crystalline powder (7.3 mg). This powder had the same physico-chemical properties as shown in Example 10.

EXAMPLE 13

METHOD FOR PREPARATION OF THE TRITYLATION PRODUCT OF ANTIBIOTIC PS-5 IN THE PRESENCE OF A QUATERNARY AMMONIUM SALT

The antibiotic PS-5 was extracted from 48 liter of broth filtrate (11.7 CCU/ml) twice with 15 liter each of dichloromethane containing 0.05% cetyldimethylbenzylammonium chloride (activity of the dichloromethane extract: 24.0 CCU/ml; activity of the spent broth filtrate: 5.7 CCU/ML).

The dichloromethane extract was dried over 400 g of anhydrous sodium sulfate and evaporated to 500 ml under reduced pressure in a rotary evaporator. The concentrate (450 CCU/ml) was dehydrated preliminarily over 10 g of anhydrous sodium sulfate and then, after filtration, with 5 g of Molecular sieves 4A (Union Carbide Corp.).

To this dry solution, 4.5 g of trityl chloride was added at a temperature below 5° C. and the mixture was stirred for 5 hours at 5° C. After removal of dichloromethane by evaporation at a room temperature, the residue was dissolved in 15 ml of benzene and purified in a similar manner as described in Example 10 to provide 8 mg of anhydrous crystalline powder of the trityl ester of the antibiotic PS-5. The physico-chemical characteristics of this preparation were almost the same as those described in Example 10.

EXAMPLE 14

ANTIBIOTIC PS-5 METHYL ESTER

Ninety milligrams of the antibiotic PS-5 sodium salt obtained in Example 9 (8,000 CCU/mg) was suspended in 3 ml of dry dimethylformamide, to which 50 mg of triethylamine and 0.3 ml of methyl iodide were added. After stirring for two and a half hours at room temperature, 100 ml of benzene were added and well mixed for extraction. The benzene layer was separated, washed with 100 ml of 0.1 M, pH 6.8, phosphate buffer and then dried over anhydrous sodium sulfate. The dry benzene solution was concentrated to a small volume under reduced pressure and applied on a Bio-Beads S-X3 (BIO-RAD Laboratories) column (1.2×90 cm).

The methyl ester was developed with benzene. Eluate fractions containing the ester were combined, and evaporated to dryness under reduced pressure to yield a colorless oil. The oily material was dissolved in a small amount of acetone and chromatographed on a Sephadex LH-20 (1.2×90 cm) column with acetone as the developing agent. Eluate fractions containing the methyl ester of the antibiotic PS-5 were collected and evaporated to dryness to yield 11.2 mg of antibiotic PS-5 methyl ester. The methyl ester exhibited the following physical and chemical properties:

(1) Thin layer chromatography

Rf=0.45(Silicagel 60 $F_{254}$ plate: benzene-acetone=1.1)

(2) Ultraviolet absorption maximum in methanol $\lambda_{max}^{CH3OH}$=315.5 nm (3) Infrared absorption maxima in chloroform 3430, 1766, 1660 cm$^{-1}$ (4) Signals in the proton magnetic resonance spectrum in deuteriochloroform (δ)

1.05 (3H, t, J=7.5 Hz)
1.7–2.0 (2H, m)
2.00 (3H, s)
2.8–3.65 (7H, m)
3.83 (3H, s)
3.84–4.06 (1H, m)

(5) Molecular weight (High resolution mass spectrometry)

312.1131 (found)
312.1143: calculated for $C_{14}H_{20}N_2O_4S$

The following structure is assigned to the methyl ester of the antibiotic PS-5 on the basis of the previously described structure of the antibiotic PS-5 and of the above specified physico-chemical data:

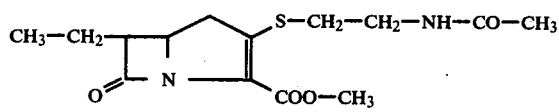

The procedure explained above in Example 14 was repeated with ethyl iodide, isopropyl iodide, isobutyl iodide, n-pentyl iodide or n-hexyl iodide instead of methyl iodide to give the following esters respectively:
antibiotic PS-5 ethyl ester
antibiotic PS-5 isopropyl ester
antibiotic PS-5 isobutyl ester
antibiotic PS-5 n-pentyl ester
antibiotic PS-5 n-hexyl ester The formation of these esters could be confirmed by thin layer chromatography, infrared absorption spectrometry, proton magnetic resonance spectrometry and mass spectrometry.

As explained before, composition containing antibiotic PS-5 and/or the trityl ester of antibiotic PS-5 may be administered in various unit dosage forms such as in solid or liquid orally ingestible dosage form. The said composition per unit dosage, whether solid or liquid, may contain the active material in an amount of 0.1–99%, preferably 10–60%. The amount of the active ingredient in the composition may change depending on the dosage form and the total weight of the composition, and usually is in the range of 10 mg to 1,000 mg, preferably 100 mg to 1,000 mg.

In parenteral administrations the unit dosage is usually the pure or highly purified antibiotic PS-5, a pharmaceutically acceptable salt and/or the tritylation product of antibiotic PS-5 in sterile water solution or in the form of a soluble powder intended for solution.

Representative formulations containing the antibiotic PS-5 and/or the tritylation product of the antibiotic PS-5 can be prepared by the following procedures:

EXAMPLE A: CAPSULES

| Component | Per capsule |
| --- | --- |
| Antibiotic PS-5 (sodium salt) | 100 mg |
| Lactose (J.P.) | a sufficient amount |
| Magnesium stearate | 1 mg |

The active compound and the diluents are well mixed to produce a uniform blend. Two hundred milligrams of the blend is filled in a No. 3 hard gelatin capsule.

EXAMPLE B: TABLETS

| Component | Per tablet |
| --- | --- |
| Antibiotic PS-5 (sodium salt) | 200 mg |
| Lactose (J.P.) | 120 mg |
| Corn starch | 175 mg |
| Magnesium stearate | 5 mg |

In the above composition, the active component is blended with lactose and a half amount of corn starch.

The mixture is granulated with 10% of the said amount of corn starch paste and screened. The balance of corn starch and magnesium stearate are added and the mixture is compressed into tablets, approximately 1 cm in diameter, each weighing 500 mg.

EXAMPLE C: LYO FORM FOR INJECTION

| Component | Per vial |
| --- | --- |
| Antibiotic PS-5 (sodium salt) | 25 mg |
| Sterile distilled water for injection (J.P.) | 2 ml |

The active component is dissolved in sterile dissolved water for injection, filtered and sterilized. The solution is subdivided into sterile vials, and water is aseptically removed by lyophilization. The vials containing the sterile dry solid are aseptically sealed.

To restore for parenteral administration, 2 ml of sterile physiological saline is added to the content of a vial.

EXAMPLE D: TABLETS

| Component | Per tablet |
| --- | --- |
| Antibiotic PS-5 (sodium salt) | 20 mg |
| Cephaloridine | 180 mg |
| Lactose (J.P.) | 120 mg |
| Corn starch | 175 mg |
| Magnesium stearate | 5 mg |
| | 500 mg |

Antibiotic PS-5 and cephaloridine are mixed with the other ingredients and compressed into tablets as described in Example B. The tablets are covered first with a sugar coating and then with an enteric coating.

EXAMPLE E: TABLETS

| Component | Per tablet |
| --- | --- |
| Antibiotic PS-5 (sodium salt) | 10 mg |
| Aminobenzylpenicillin | 190 mg |
| Lactose | 120 mg |
| Corn Starch | 175 mg |
| Magnesium stearate | 5 mg |
| | 500 mg |

The tablets containing antibiotic PS-5 and aminobenzylpenicillin are obtained by the same method as described in Example B.

EXAMPLE F: CAPSULES

| Component | Per capsule |
| --- | --- |
| Trityl ester of antibiotic PS-5 | 100 mg |
| Lactose | a sufficient quantity |
| Magnesium stearate | 1 mg |

The active ingredient and diluents are well mixed to give a uniform blend. About 200 mg each of the blend is filled in a No. 3 hard capsule.

EXAMPLE G: TABLETS

| Component | Per tablet |
|---|---|
| Trityl ester of antibiotic PS-5 | 200 mg |
| Lactose (J.P.) | 120 mg |
| Corn starch | 175 mg |
| Magnesium stearate | 5 mg |
| | 500 mg |

In the above example, the active ingredient is blended with lactose and a half amount of corn starch in the indicated ratio. The mixture is granulated with 10% of the indicated amount of corn starch, and sieved. Magnesium stearate and the balance of corn starch are added and the mixture is compressed into tablets of 1 cm in diameter, each weighing 500 mg. The tablets are covered first with a sugar coating and then with an enteric coating.

EXAMPLE H: LYO FORM FOR INJECTION

| Component | Per vial |
|---|---|
| Trityl ester of antibiotic PS-5 | 25 mg |
| Sterile distilled water for injection (J.P.) | 2 ml |

The active component is dissolved in sterile distilled water for injection and sterilized by filtration. The solution is subdivided in vials and aseptically freeze-dried. The vials containing the sterile dry solid are aseptically sealed.

On injection, 2 ml of sterile 70% N-(beta-hydroxyethyl)-lactamide is added to the content of a vial.

EXAMPLE I: TABLETS

| Component | Per tablet |
|---|---|
| Trityl ester of antibiotic PS-5 | 50 mg |
| Caphaloridine | 150 mg |
| Lactose (J.P.) | 120 mg |
| Corn starch | 175 mg |
| Magnesium stearate | 5 mg |
| | 500 mg |

The trityl ester of antibiotic PS-5 and cephaloridine are mixed and then by the same method as described in Example G, compressed into tablets and coated.

EXAMPLE J: TABLETS

| Component | Per tablet |
|---|---|
| Trityl ester of antibiotic PS-5 | 20 mg |
| Aminobenzylpenicillin | 180 mg |
| Lactose (J.P.) | 120 mg |
| Corn starch | 175 mg |
| Magnesium stearate | 5 mg |
| | 500 mg |

The active ingredients (the trityl ester of antibiotic PS-5 and aminobenzylpenicillin) are mixed and processed by the same method as described in Example I.

We claim:

1. A compound selected from PS-5 and the salts and esters thereof, the compound corresponding to the formula

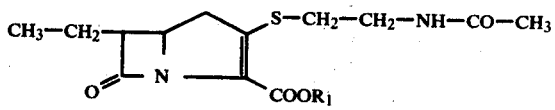

(A)

wherein $R_1$ represents hydrogen, lower alkyl and triphenylmethyl, and including the salts of the compound wherein $R_1$ is hydrogen.

2. A compound of claim 1 wherein $R_1$ is hydrogen.
3. A compound of claim 1 wherein $R_1$ is triphenylmethyl.
4. A compound of claim 1 wherein $R_1$ is methyl.
5. A compound of claim 1 which is a pharmaceutically acceptable salt of the compound wherein $R_1$ is hydrogen.
6. A compound of claim 1 which is the sodium salt of the compound wherein $R_1$ is hydrogen.
7. The sodium salt of the compound of claim 6 in essentially pure form.
8. An antibiotically effective composition comprising a suitable pharmaceutical carrier and, as an active ingredient, a compound selected from PS-5 and the salts and esters thereof, the compound corresponding to the formula

(A)

wherein $R_1$ represents hydrogen, lower alkyl and triphenylmethyl, and including the salts of the compound wherein $R_1$ is hydrogen.

9. A composition of claim 8 wherein the active ingredient is a pharmaceutically acceptable salt of the compound wherein $R_1$ is hydrogen.
10. A composition of claim 8 wherein the active ingredient is the compound wherein $R_1$ is triphenylmethyl.
11. A composition according to claims 8, 9 or 10 wherein the active ingredient is contained in an antibiotically effective amount.
12. A method for combatting or preventing a bacterial infection in mammals which comprises administering to the mammal an antibiotically effective amount of a compound selected from PS-5 and the pharmaceutically-acceptable salts and esters thereof, the compound corresponding to the formula

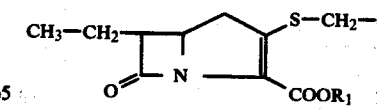

(A)

wherein $R_1$ represents hydrogen, lower alkyl and triphenylmethyl, and including the pharmaceutically-acceptable salts of the compound wherein $R_1$ is hydrogen.

13. Method of claim 12 wherein $R_1$ is triphenylmethyl.

14. Method of claim 12 wherein the compound is a pharmaceutically-acceptable salt of PS-5, being a pharmaceutically-acceptable salt of the compound wherein $R_1$ is hydrogen.

15. Method of claim 14 wherein said salt is the sodium salt of PS-5.

* * * * *

UNITED STATES PATENT AND TRADEMARK OFFICE
CERTIFICATE OF CORRECTION

PATENT NO. : 4,318,916

DATED : March 9, 1982

INVENTOR(S) : Kazuhiko Okamura, et al.

It is certified that error appears in the above—identified patent and that said Letters Patent is hereby corrected as shown below:

Column 1, line 17, "67221W;" should read --67721W;--.

Column 3, Table 1, between lines 15 and 20, under subheading, Color of Aerial Mycelium, after "light orange" please insert --yellow (3 ea)--.

Column 5, Table 4, under subheading "Carbon Sourses" first line, "Arabinose" should read --L-Arabinose--.

Column 6, line 58, "80" should read --30--.

Column 9, line 47, "10;14 40" should read --10 - 40--.

Column 10, line 14, "$CH_2$-)" should read --$\underline{C}H_2$-)--.

Column 18, line 63, "of the" should read --to be--.

Column 28, line 20, "Hz)($CH_3$" should read --Hz)($\underline{C}H_3$--.

Column 28, line 22, "$CH_2$" should read --$\underline{C}H_2$--.

Column 30, line 52, Table 8, under subheading Microorganism, "EDA" should read --FDA--.

UNITED STATES PATENT AND TRADEMARK OFFICE
CERTIFICATE OF CORRECTION

PATENT NO. : 4,318,916

DATED : March 9, 1982

INVENTOR(S) : Kazuhiko Okamura, et al.

It is certified that error appears in the above—identified patent and that said Letters Patent is hereby corrected as shown below:

Column 39, Table 16, Stock solution No. 3, under sub-heading Trityl PS-5: cephaloridine, should read --50:1000--.

Column 39, Table 16, Stock solution No. 5, under sub-heading Trityl PS-5: cephaloridine, should read --0:2000--.

Column 41, line 56, "(7.3 mg)." should read --(17.3 mg).--.

Column 42, line 52, "1.1" should read --1:1--.

Column 46, Claim 1, line 5, before the formula take out the (A).

Column 46, Claim 8, line 34, before the formula take out (A).

Column 46, Claim 12, line 60, before the formula take out (A).

Signed and Sealed this

Eighth Day of February 1983

[SEAL]

Attest:

GERALD J. MOSSINGHOFF

Attesting Officer  Commissioner of Patents and Trademarks

UNITED STATES PATENT AND TRADEMARK OFFICE
CERTIFICATE OF CORRECTION

PATENT NO. : 4,318,916

DATED : March 9, 1982

INVENTOR(S) : Kazuhiko Okamura, et al.

It is certified that error appears in the above—identified patent and that said Letters Patent is hereby corrected as shown below:

Title page of the above patent, next to [73] Assignee: please add --Panlabs Inc., Fayetteville, New York--.

Signed and Sealed this

Twenty-first Day of June 1983

[SEAL]

Attest:

DONALD J. QUIGG

Attesting Officer

Acting Commissioner of Patents and Trademarks